United States Patent
Sasaki et al.

(10) Patent No.: US 12,384,903 B2
(45) Date of Patent: Aug. 12, 2025

(54) RESIN COMPOSITION, LIQUID COMPOSITION, COLORING AGENT COMPOUND, AND OPTICAL MATERIAL

(71) Applicant: FUJIFILM CORPORATION, Tokyo (JP)

(72) Inventors: Daisuke Sasaki, Shizuoka (JP); Yoshihiro Jimbo, Shizuoka (JP); Hidetomo Furuyama, Shizuoka (JP)

(73) Assignee: FUJIFILM CORPORATION, Tokyo (JP)

( * ) Notice: Subject to any disclaimer, the term of this patent is extended or adjusted under 35 U.S.C. 154(b) by 960 days.

(21) Appl. No.: 17/511,567

(22) Filed: Oct. 27, 2021

(65) Prior Publication Data

US 2022/0049068 A1 Feb. 17, 2022

Related U.S. Application Data

(63) Continuation of application No. PCT/JP2020/020291, filed on May 22, 2020.

(30) Foreign Application Priority Data

May 23, 2019 (JP) ................................. 2019-096563

(51) Int. Cl.

| | |
|---|---|
| C08K 5/3415 | (2006.01) |
| C07D 403/06 | (2006.01) |
| C07D 405/14 | (2006.01) |
| C07D 413/06 | (2006.01) |
| C08L 57/00 | (2006.01) |
| C08L 101/00 | (2006.01) |
| C09B 23/04 | (2006.01) |
| C09D 133/12 | (2006.01) |
| G02B 1/04 | (2006.01) |
| G02B 1/14 | (2015.01) |
| G02B 5/22 | (2006.01) |
| G02C 7/00 | (2006.01) |
| G02C 7/10 | (2006.01) |

(52) U.S. Cl.
CPC ............ C08K 5/3415 (2013.01); C08L 57/00 (2013.01); G02B 1/14 (2015.01)

(58) Field of Classification Search
None
See application file for complete search history.

(56) References Cited

U.S. PATENT DOCUMENTS

| 5,296,344 A | 3/1994 | Jmbo et al. |
| 6,187,929 B1 | 2/2001 | Fukuda et al. |
| 2018/0355149 A1 | 12/2018 | Sasaki |

FOREIGN PATENT DOCUMENTS

| EP | 967517 A1 * | 12/1999 | ............ C09B 23/02 |
| JP | 2681525 B2 | 11/1997 | |
| JP | 2707371 B2 | 1/1998 | |
| JP | 11193352 A * | 7/1999 | |
| JP | 11193353 A * | 7/1999 | |
| JP | H11-193352 A | 7/1999 | |
| JP | H11-193353 A | 7/1999 | |
| JP | 2000-080296 A | 3/2000 | |
| JP | 2002207268 A * | 7/2002 | |
| JP | 2009-210929 A | 9/2009 | |
| WO | 2017/086245 A1 | 5/2017 | |
| WO | 2017/145637 A1 | 8/2017 | |

OTHER PUBLICATIONS

Belezheva et al., "Synthesis and Properties of Some Lewis and Bronsted Acids of the Indole Series," D.I Mendeleeve Moscow Instittue of Chemical Technology, Moscow 125047, pp. 1088-1093. Translated from Khimiya Geterotsiklicheskikh Soedinenii, No. 10, pp. 1343-1348, (1978) (Year: 1978).*

Xu-Yao Zhang et al., "Synthesis, in vitro and in vivo anticancer activities of novel 4-substituted 1,2-bis4-chlorophenyl)-pyrazolidine-3,5-dione derivatives", Med. Chem. Commun., vol. 6, Royal Society of Chemistry, Aug. 12, 2015, p. 1781-1786.

Velezheva, V. S. et al., "Synthesis and Properties of Some Lewis and Bronsted Acids of the Indole Series", Khimiya Geterotsiklicheskikh Soedinenii, vol. 10, Dec. 31, 1978, p. 1343-1348.

English language translation of the following: Office action dated Sep. 7, 2023 from the SIPO in a Chinese patent application No. 202080035986.X corresponding to the instant patent application. This office action translation is submitted now in order to supplement the understanding of the cited references which are being disclosed in the instant Information Disclosure Statement.

Zhang, Xu-Yao, et al., "Synthesis, in vitro and in vivo anticancer activities of novel 4-substituted 1, 2-bis (4-chlorophenyl )-pyrazolidine-3, 5-dione derivatives", MedChemComm, 2015, 6(10), p. 1781-p. 1786 Table 1, compound 4v.

(Continued)

*Primary Examiner* — Ha S Nguyen
(74) *Attorney, Agent, or Firm* — SOLARIS Intellectual Property Group, PLLC

(57) ABSTRACT

Provided are a resin composition including a coloring agent represented by Formula 1 and a resin; a liquid composition; a coloring agent compound; and an optical material. In Formula 1, $R^1$ and $R^2$ each independently represent an alkyl group or an aryl group, $R^3$, $R^4$, $R^5$, and $R^6$ each independently represent a hydrogen atom or a substituent, and $R^5$ and $R^6$ may be bonded to each other to form a 6-membered ring.

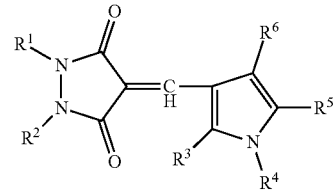

Formula 1

8 Claims, No Drawings

(56) References Cited

OTHER PUBLICATIONS

Velezheva, V. S. et al., "Khimiya Geterotsiklicheskikh Soedinenii", 10, 1978, p. 1343-p. 1348, p. 1343, compound IV, p1346 compound XVI.
International Search Report issued in International Application No. PCT/JP2020/020291 on Jul. 21, 2020.
Written Opinion of the ISA issued in International Application No. PCT/JP2020/020291 on Jul. 21, 2020.
English language translation of the following: Office action dated Jun. 21, 2022 from the JPO in a Japanese patent application No. 2021-520875 corresponding to the instant patent application.

* cited by examiner

RESIN COMPOSITION, LIQUID COMPOSITION, COLORING AGENT COMPOUND, AND OPTICAL MATERIAL

CROSS-REFERENCE TO RELATED APPLICATIONS

This application is a continuation application of International Application No. PCT/JP2020/020291, filed May 22, 2020, the disclosure of which is incorporated herein by reference in its entirety. Further, this application claims priority from Japanese Patent Application No. 2019-096563, filed May 23, 2019, the disclosure of which is incorporated herein by reference in its entirety.

BACKGROUND OF THE INVENTION

1. Field of the Invention

The present disclosure relates to a resin composition, a liquid composition, a coloring agent compound, and an optical material.

2. Description of the Related Art

It is concerned that ultraviolet rays in a wavelength range from the visible light region to the short wavelength side, and blue light emitted from displays of various image display apparatuses, and the like may affect the human body (particularly, eyes).

With regard to the ultraviolet rays (UV), UV-cutting materials such as glass, films, and spectacle lenses formed of a component which absorbs the ultraviolet rays, and daily necessities such as cosmetics for UV care and sunblocks have been provided.

In addition, in recent years, attention has been paid to the effect of blue light included in light emitted from a display of an image display apparatus such as a liquid crystal display device or a display of a mobile device such as a smartphone on the eyes, and eye strain caused by the blue light is regarded as a problem. Therefore, a spectacle lens or a protective film using a component which absorbs the blue light has been proposed not only for the ultraviolet rays but also for blue light having a wavelength of 380 nm to 500 nm.

On the other hand, as an example of a dye used for dyeing a layer of a silver halide photographic photosensitive material, a compound having a pyrazolone ring and an indole ring in the molecular structure has been disclosed (for example, see JP2707371B). In addition, as a dye used for the same purpose, a compound having a pyrazolidinedione skeleton has been disclosed (for example, see JP2681525B and JP1999-193353A (JP-H11-193353A)). In JP1999-193353A (JP-H11-193353A), in a case where an oil-soluble dye has a portion where a hydrogen atom on a nitrogen atom dissociates, hydrophilicity of the entire molecule is high during an alkaline color development treatment, and excellent decolorization is exhibited.

On the other hand, a material, in which a component responsible for absorbing the ultraviolet rays and the blue light is used, is usually used in an environment which is continuously exposed to light such as sunlight or in a high temperature environment, for example, spectacle lenses and glass windows of vehicles. Therefore, it is desired that the component responsible for absorbing the ultraviolet rays and the blue light has a certain degree of fastness against light and heat.

SUMMARY OF THE INVENTION

In the related art, techniques for blocking ultraviolet rays and blue light have been studied. However, a coloring agent which can obtain high absorbance in a wavelength range of 280 nm to 500 nm and can stably maintain the high absorbance even in a case of being placed in a light-exposed environment or a high-temperature environment is in a situation where the coloring agent has not always been provided. A coloring agent that can withstand use in an environment which can be continuously exposed to light and heat (for example, an outdoor environment) is expected to be widely used for those that are used or installed outdoors.

The coloring agents disclosed in JP2707371B, JP2681525B, and JP1999-193353A (JP-H11-193353A) described above are intended for dyeing a layer of a silver halide photographic photosensitive material, and are considered to be effective in that it is structurally excellent in decolorization after dyeing. However, it is presumed that there is still room for improvement in blocking ability of ultraviolet rays and blue light having an absorption wavelength on the shorter wavelength side than the visible region.

The present disclosure has been made in view of the above.

An object to be achieved by embodiments of the present disclosure is to provide a resin composition and a liquid composition which have high absorbance in a wavelength range of at least 350 nm to 450 nm and are excellent in light resistance and heat resistance.

An object to be achieved by other embodiments of the present disclosure is to provide a novel coloring agent compound which has high absorbance in a wavelength range of at least 350 nm to 450 nm and is excellent in light resistance and heat resistance.

An object to be achieved by other embodiments of the present disclosure is to provide an optical material which has high absorbance in a wavelength range of at least 350 nm to 450 nm and is suitable for use in light-exposed and high-temperature environments.

The specific methods for achieving the objects include the following aspects.

<1> A resin composition comprising:
a coloring agent represented by Formula 1; and
a resin.

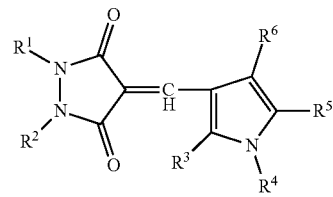

Formula 1

In Formula 1, $R^1$ and $R^2$ each independently represent an alkyl group or an aryl group, $R^3$, $R^4$, $R^5$, and $R^6$ each independently represent a hydrogen atom or a substituent, and $R^5$ and $R^6$ may be bonded to each other to form a 6-membered ring.

<2> The resin composition according to <1>, in which $R^1$ represents an alkyl group, and $R^2$ represents an alkyl group or an aryl group.

<3> The resin composition according to <1> or <2>, in which $R^1$ and $R^2$ each independently represent an alkyl group.

<4> The resin composition according to <1>,
in which $R^1$ and $R^2$ each independently represent an aryl group,
$R^3$, $R^5$, and $R^6$ each independently represent a hydrogen atom, an alkyl group, or an aryl group, and
at least one of $R^3$ or $R^6$ represents a hydrogen atom.
<5> A liquid composition comprising:
a coloring agent represented by Formula 1; and
a solvent.

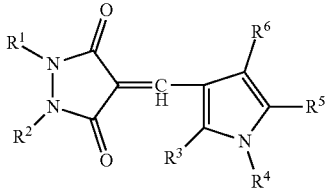

Formula 1

In Formula 1, $R^1$ and $R^2$ each independently represent an alkyl group or an aryl group, $R^3$, $R^4$, $R^5$, and $R^6$ each independently represent a hydrogen atom or a substituent, and $R^5$ and $R^6$ may be bonded to each other to form a 6-membered ring.

<6> The liquid composition according to <5>,
in which $R^1$ represents an alkyl group, and $R^2$ represents an alkyl group or an aryl group.
<7> The liquid composition according to <5> or <6>,
in which $R^1$ and $R^2$ each independently represent an alkyl group.
<8> The liquid composition according to <5>,
in which $R^1$ and $R^2$ each independently represent an aryl group,
$R^3$, $R^5$, and $R^6$ each independently represent a hydrogen atom, an alkyl group, or an aryl group, and
at least one of $R^3$ or $R^6$ represents a hydrogen atom.
<9> The liquid composition according to any one of <5> to <8>,
in which the liquid composition is used for an ink or a paint.
<10> A coloring agent compound represented by Formula 2.

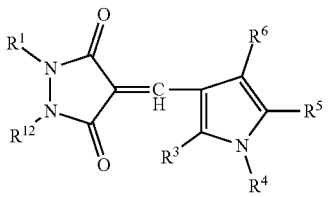

Formula 2

In Formula 2, $R^1$ represents an alkyl group or an aryl group,
in a case where $R^1$ represents an alkyl group, $R^{12}$ represents an alkyl group or an aryl group, $R^3$, $R^5$, and $R^6$ each independently represent a hydrogen atom, an alkyl group, or an aryl group, $R^4$ represents a hydrogen atom, an alkyl group, an aryl group, or an amino group, and $R^5$ and $R^6$ may be bonded to each other to form a 6-membered ring,
in a case where $R^1$ represents an aryl group, $R^{12}$ represents an aryl group, $R^3$, $R^5$, and $R^6$ each independently represent a hydrogen atom, an alkyl group, or an aryl group, at least one of $R^3$ or $R^6$ represents a hydrogen atom, $R^4$ represents a hydrogen atom, an alkyl group, an aryl group, or an amino group, and $R^5$ and $R^6$ may be bonded to each other to form a 6-membered ring, and a case where the aryl group in $R^1$ and $R^{12}$ is substituted with a group having a sulfonamide structure is excluded.

<11> The coloring agent compound according to <10>,
in which $R^1$ and $R^{12}$ each independently represent an alkyl group.
<12> An optical material which is a cured substance of the resin composition according to any one of <1> to <4> or the liquid composition according to any one of <5> to <8>.
<13> An optical material comprising:
a coloring agent represented by Formula 1.

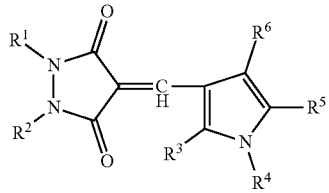

Formula 1

In Formula 1, $R^1$ and $R^2$ each independently represent an alkyl group or an aryl group, $R^3$, $R^4$, $R^5$, and $R^6$ each independently represent a hydrogen atom or a substituent, and $R^5$ and $R^6$ may be bonded to each other to form a 6-membered ring.

<14> The optical material according to <12> or <13>,
in which the optical material is a spectacle lens.
<15> The optical material according to <12> or <13>,
in which the optical material is a protective sheet.

According to the embodiments of the present disclosure, a resin composition and a liquid composition, which have high absorbance in a wavelength range of at least 350 nm to 450 nm and are excellent in light resistance and heat resistance, are provided.

According to the embodiments of the present disclosure, a novel coloring agent compound, which has high absorbance in a wavelength range of at least 350 nm to 450 nm and is excellent in light resistance and heat resistance, is provided.

According to the embodiments of the present disclosure, an optical material, which has high absorbance in a wavelength range of at least 350 nm to 450 nm and is suitable for use in light-exposed and high-temperature environments, is provided.

DESCRIPTION OF THE PREFERRED EMBODIMENTS

Hereinafter, the content of the present disclosure will be described in detail.

The configuration requirements will be described below based on the representative embodiments of the present disclosure, but the present disclosure is not limited to such embodiments.

In the present disclosure, a term "to" showing a range of numerical values is used as a meaning including a lower limit value and an upper limit value disclosed before and after the term.

In a range of numerical values described in stages in the present disclosure, the upper limit value or the lower limit value described in one range of numerical values may be replaced with an upper limit value or a lower limit value of the range of numerical values described in other stages. In addition, in a range of numerical values described in the present disclosure, the upper limit value or the lower limit value of the range of numerical values may be replaced with values shown in the examples.

In the present disclosure, a compound which is not specifically described as substituted or unsubstituted may have an optional substituent as long as the effect in the present disclosure is not impaired.

In the present disclosure, in a case where a plurality of substances corresponding to components are present in a layer, an amount of each component in the composition means a total amount of the plurality of substances present in the composition, unless otherwise noted.

In the present disclosure, a combination of preferred aspects is a more preferred aspect.

<Resin Composition>

A resin composition according to an embodiment of the present disclosure includes a coloring agent represented by Formula 1 described later (hereinafter, also referred to as a specific coloring agent), and a resin. The resin composition according to the embodiment of the present disclosure may further include a coloring agent other than the specific coloring agent, an ultraviolet absorber, and other components, as necessary.

It has been found that a coloring agent, as represented by Formula 1, having a structure in which a pyrazolidinedione skeleton and a pyrrole skeleton are linked by a methine group has high absorption especially in a wavelength range of 350 nm to 450 nm, and is fast to heat and light.

Since the resin composition according to the embodiment of the present disclosure includes the specific coloring agent, as shown in Formula 1, having a structure in which a pyrazolidinedione skeleton and a pyrrole skeleton are linked by a methine group, the resin composition according to the embodiment of the present disclosure has high absorbance for wavelength light of at least 350 nm to 450 nm, and is excellent in light resistance and heat resistance. Therefore, by using the resin composition according to the embodiment of the present disclosure, a resin body having high absorbance for wavelength light of at least 350 nm to 450 nm and having excellent light resistance and heat resistance can be obtained by a known molding method. Specifically, for example, it is possible to provide a material which blocks or suppresses ultraviolet rays (UV) and blue light (for example, a molded product such as glass, a film, a sheet, a lens).

(Coloring Agent)

The resin composition according to the embodiment of the present disclosure includes a coloring agent represented by Formula 1 (that is, the specific coloring agent).

The coloring agent represented by Formula 1 (that is, the specific coloring agent) is a yellow coloring agent having high absorbance for at least a wavelength range of 350 nm to 450 nm in a wavelength range of 280 nm to 500 nm. Further, it is preferable to be a yellow coloring agent having high absorbance for a wavelength range of 380 nm to 450 nm.

The specific coloring agent in the present disclosure includes a dye and a pigment.

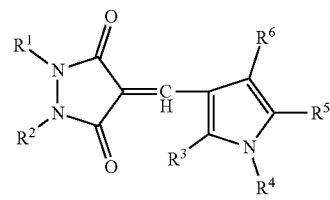

Formula 1

In Formula 1, $R^1$ and $R^2$ each independently represent an alkyl group or an aryl group, $R^3$, $R^4$, $R^5$, and $R^6$ each independently represent a hydrogen atom or a substituent, and $R^5$ and $R^6$ may be bonded to each other to form a 6-membered ring.

The alkyl group in $R^1$ and $R^2$ may be either an unsubstituted alkyl group or a substituted alkyl group substituted with a substituent.

As the unsubstituted alkyl group, an alkyl group having 1 to 12 carbon atoms is preferable and an alkyl group having 1 to 6 carbon atoms is more preferable, and examples thereof include a methyl group, an ethyl group, a normal propyl group, an isopropyl group, and a cyclohexyl group.

Examples of the substituent of the substituted alkyl group include substituents included in the following substituent group A.

(Substituent Group A)

halogen atom, alkyl group, cycloalkyl group, aralkyl group, alkenyl group, alkynyl group, aryl group, heterocyclic group, cyano group, hydroxy group, nitro group, carboxy group (may be in a form of salt), alkoxy group, aryloxy group, silyloxy group, heterocyclic oxy group, acyloxy group, carbamoyloxy group, sulfonyloxy group, alkoxycarbonyloxy group, aryloxycarbonyloxy group, amino group, anilino group, alkylamino group, acylamino group, aminocarbonylamino group, alkylcarbonylamino group, alkoxycarbonylamino group, aryloxycarbonylamino group, sulfamoylamino group, alkylsulfonylamino group, arylsulfonylamino group, sulfonamide group, mercapto group, alkylthio group, arylthio group, heterocyclic thio group, sulfamoyl group, sulfo group (may be in a form of salt), alkylsulfinyl group, arylsulfinyl group, alkylsulfonyl group, arylsulfonyl group, acyl group, aryloxycarbonyl group, alkoxycarbonyl group, carbamoyl group, imide group, phosphino group, phosphinyl group, phosphinyloxy group, phosphinylamino group, silyl group, and the like Among the substituent group A, preferred examples of the substituent of the substituted alkyl group include a halogen atom, an alkyl group, an aryl group, an alkoxy group, an acyl group, and a hydroxy group.

As the substituted alkyl group substituted with a substituent, a substituted alkyl group having 1 to 12 total carbon atoms is preferable, and examples thereof include a benzyl group, a hydroxybenzyl group, and a methoxyethyl group.

In a case where both $R^1$ and $R^2$ represent an alkyl group, the alkyl groups may be the same or different from each other.

The aryl group in $R^1$ and $R^2$ may be either an unsubstituted aryl group or a substituted aryl group substituted with a substituent.

As the unsubstituted aryl group, an aryl group having 6 to 12 carbon atoms is preferable, and examples thereof include a phenyl group.

Examples of the substituent of the substituted aryl group include substituents included in the above-described substituent group A.

Preferred examples of the substituent of the substituted aryl group include a halogen atom (for example, a chlorine atom, a bromine atom, and an iodine atom), a hydroxy group, a carboxy group, a sulfonamide group, an amino group, an alkyl group (preferably, an alkyl group having 1 to 4 carbon atoms; for example, a methyl group, an ethyl group, a normal propyl group, and an isopropyl group), an alkoxy group (preferably, an alkoxy group having 1 to 4 carbon atoms; for example, a methoxy group, an ethoxy group, a normal propoxy group, and an isopropoxy group), an alkoxycarbonyl group (preferably, an alkoxycarbonyl group having 2 to 5 carbon atoms; for example, a methoxycarbonyl group, an ethoxycarbonyl group, a normal propoxycarbonyl group, and an isopropoxycarbonyl group), a sulfonyloxy group, and a monovalent group in which at least two of these groups are linked.

As the substituted aryl group substituted with a substituent, an aryl group having 6 to 18 total carbon atoms is preferable, and examples thereof include a 4-chlorophenyl group, a 2,5-dichlorophenyl group, a hydroxyphenyl group, a 4-carboxyphenyl group, a 3,5-dicarboxyphenyl group, a 4-methanesulfonamide phenyl group, a 4-methylphenyl group, a 4-methoxyphenyl group, a 4-(2-hydroxyethoxy) phenyl group, an N,N-dimethylaminophenyl group, a 4-(N-carboxymethyl-N-ethylamino)phenyl group, a 4-ethoxycarbonylphenyl group, and a 4-methanesulfonyloxyphenyl group.

In a case where both $R^1$ and $R^2$ represent an aryl group, the aryl groups may be the same or different from each other.

Examples of the substituents in $R^3$, $R^4$, $R^5$, and $R^6$ include substituents included in the above-described substituent group A.

Among the substituent group A, $R^3$, $R^5$, and $R^6$ are preferably an alkyl group or an aryl group.

It is preferable that $R^3$, $R^5$, and $R^6$ each independently represent a hydrogen atom, an alkyl group, or an aryl group.

Among the substituent group A, $R^4$ is preferably an alkyl group, an aryl group, or an amino group.

It is preferable that $R^4$ represents a hydrogen atom, an alkyl group, an aryl group, or an amino group.

The alkyl group in $R^3$, $R^5$, and $R^6$ may be either an unsubstituted alkyl group or a substituted alkyl group substituted with a substituent.

As the unsubstituted alkyl group, an alkyl group having 1 to 8 carbon atoms is preferable and an alkyl group having 1 to 4 carbon atoms is more preferable, and examples thereof include a methyl group, an ethyl group, a normal propyl group, and an isopropyl group.

Examples of the substituent of the substituted alkyl group in $R^3$, $R^5$, and $R^6$ include substituents included in the above-described substituent group A.

Preferred examples of the substituent of the substituted alkyl group include a phenyl group, a carboxy group, and a hydroxy group.

As the substituted alkyl group substituted with a substituent, an alkyl group having 1 to 8 total carbon atoms is preferable, and examples thereof include a benzyl group, a carboxymethyl group, and a hydroxymethyl group.

In a case where all $R^3$, $R^5$, and $R^6$ represent an alkyl group, the alkyl groups may be the same or different from each other.

The aryl group in $R^3$, $R^5$, and $R^6$ may be either an unsubstituted aryl group or a substituted aryl group substituted with a substituent.

As the unsubstituted aryl group, an aryl group having 6 to 10 carbon atoms is preferable, and examples thereof include a phenyl group.

Examples of the substituent of the substituted aryl group in $R^3$, $R^5$, and $R^6$ include substituents included in the above-described substituent group A.

Preferred examples of the substituent of the substituted aryl group include a halogen atom (for example, a chlorine atom, a bromine atom, and an iodine atom), a hydroxy group, a carboxy group, and an alkyl group (preferably, an alkyl group having 1 to 4 carbon atoms; for example, a methyl group, an ethyl group, a normal propyl group, and an isopropyl group).

As the substituted aryl group substituted with a substituent, an aryl group having 6 to 10 total carbon atoms is preferable, and examples thereof include a 4-chlorophenyl group, a 2,5-dichlorophenyl group, a hydroxyphenyl group, a carboxyphenyl group, a 3,5-dicarboxyphenyl group, and a 4-methylphenyl group.

In a case where $R^5$ and $R^6$ are substituents, from the viewpoint of light resistance and heat resistance, $R^3$ is preferably a hydrogen atom.

In a case where all $R^3$, $R^5$, and $R^6$ represent an aryl group, the aryl groups may be the same or different from each other.

The alkyl group in $R^4$ may be either an unsubstituted alkyl group or a substituted alkyl group substituted with a substituent.

As the unsubstituted alkyl group, an alkyl group having 1 to 8 carbon atoms is preferable and an alkyl group having 1 to 4 carbon atoms is more preferable, and examples thereof include a methyl group, an ethyl group, a normal propyl group, an isopropyl group, and a cyclohexyl group.

Examples of the substituent of the substituted alkyl group in $R^4$ include substituents included in the above-described substituent group A.

Preferred examples of the substituent of the substituted alkyl group include a phenyl group, a carboxy group, a hydroxy group, an alkyl group (preferably, an alkyl group having 1 to 4 carbon atoms; for example, a methyl group, an ethyl group, a normal propyl group, and an isopropyl group), an alkoxy group (preferably, an alkoxy group having 1 to 4 carbon atoms; for example, a methoxy group, an ethoxy group, a normal propoxy group, and an isopropoxy group), an alkoxycarbonyl group (preferably, an alkoxycarbonyl group having 2 to 5 carbon atoms; for example, a methoxycarbonyl group, an ethoxycarbonyl group, a normal propoxycarbonyl group, and an isopropoxycarbonyl group), an alkylamino group (preferably, an alkylamino group having 1 to 4 carbon atoms; for example, a dimethylamino group), an alkylcarbonylamino group (preferably, an alkylcarbonylamino group having 1 to 4 carbon atoms; for example, a methylcarbonylamino group), a cyano group, and a monovalent group in which at least two of these groups are linked.

As the substituted alkyl group substituted with a substituent, an alkyl group having 1 to 18 total carbon atoms is preferable, and examples thereof include a benzyl group, a carboxybenzyl group, a hydroxybenzyl group, a methoxycarbonylethyl group, an ethoxycarbonylmethyl group, a 2-cyanoethyl group, a 2-propionylaminoethyl group, a dimethylaminomethyl group, a methylcarbonylaminopropyl group, a di(methoxycarbonylmethyl)aminopropyl group, and a phenacyl group.

The aryl group in $R^4$ may be either an unsubstituted aryl group or a substituted aryl group substituted with a substituent.

As the unsubstituted aryl group, an aryl group having 6 to 12 carbon atoms is preferable, and examples thereof include a phenyl group.

Examples of the substituent of the substituted aryl group in $R^4$ include substituents included in the above-described substituent group A.

Preferred examples of the substituent of the substituted aryl group include a halogen atom (for example, a chlorine atom, a bromine atom, and an iodine atom), a hydroxy group, a carboxy group, a sulfonamide group, an amino group, an alkyl group (preferably, an alkyl group having 1 to 4 carbon atoms; for example, a methyl group, an ethyl group, a normal propyl group, and an isopropyl group), an alkoxy group (preferably, an alkoxy group having 1 to 4 carbon atoms; for example, a methoxy group, an ethoxy group, a normal propoxy group, and an isopropoxy group), an alkoxycarbonyl group (preferably, an alkoxycarbonyl group having 2 to 5 carbon atoms; for example, a methoxycarbonyl group, an ethoxycarbonyl group, a normal propoxycarbonyl group, and an isopropoxycarbonyl group), a sulfonyloxy group, and a monovalent group in which at least two of these groups are linked.

As the substituted aryl group substituted with a substituent, an aryl group having 6 to 22 total carbon atoms is preferable, and examples thereof include a 4-chlorophenyl group, a 2,5-dichlorophenyl group, a hydroxyphenyl group, a 2,5-methoxyphenyl group, a 2-methoxy-5-ethoxycarbonylphenyl group, a 4-methoxycarbonylphenyl group, a 4-ethoxycarbonylphenyl group, a 4-butoxycarbonylphenyl group, a 4-octyloxycarbonylphenyl group, a 4-carboxyphenyl group, a 3,5-dicarboxyphenyl group, a 4-methanesulfonamide phenyl group, a 4-methylphenyl group, a 4-methoxyphenyl group, a 4-ethoxyphenyl group, a 4-(2-hydroxyethoxy) phenyl group, an N,N-dimethylaminophenyl group, an N,N-diethylaminophenyl group, a 4-(N-carboxymethyl-N-ethylamino)phenyl group, a 4-{N,N-di(ethoxycarbonylmethyl)amino}phenyl group, 4-{di(ethoxycarbonylmethyl)amino}carbonylphenyl, a 4-ethoxycarbonylphenyl group, a 4-methanesulfonyloxyphenyl group, 4-acetyl sulfamoylphenyl, 4-propionyl sulfamoylphenyl, and 4-methanesulfonamide phenyl.

The amino group in $R^4$ may be either an unsubstituted amino group or a substituted amino group substituted with a substituent.

As the substituent of the substituted amino group, the same group as the substituent of the substituted alkyl group can be mentioned.

As the substituted amino group, an alkylamino group in which one or two hydrogen atoms of the amino group are replaced with an alkyl group is preferable.

As the alkylamino group, an alkylamino group having 1 to 8 carbon atoms is preferable and an alkylamino group having 1 to 4 carbon atoms is more preferable, and examples thereof include a methylamino group, a dimethylamino group, a diethylamino group, and a pyrrolizino group.

$R^5$ and $R^6$ may be bonded to each other to form a 6-membered ring.

The 6-membered ring formed by bonding $R^5$ and $R^6$ to each other is preferably a benzene ring.

In particular, from the viewpoint of light resistance, it is preferable that $R^1$ of $R^1$ and $R^2$ in Formula 1 is an alkyl group. It is more preferable that $R^1$ represents an alkyl group and $R^2$ represents an alkyl group or an aryl group. For the same reason, it is still more preferable that both $R^1$ and $R^2$ independently represent an alkyl group, and it is particularly preferable that both $R^1$ and $R^2$ independently represent an alkyl group having 1 to 8 carbon atoms.

In addition, from the viewpoint of heat resistance and light resistance, it is also preferable that both $R^1$ and $R^2$ of $R^1$ and $R^2$ in Formula 1 are aryl groups.

It is preferable that, in a case where $R^1$ and $R^2$ each independently represent an aryl group, $R^3$, $R^5$, and $R^6$ each independently represent a hydrogen atom, an alkyl group, or an aryl group and at least one of $R^3$ or $R^6$ represents a hydrogen atom. Among these, from the viewpoint of heat resistance and light resistance, it is more preferable that $R^3$ represents a hydrogen atom and $R^5$ and $R^6$ each independently represent an alkyl group or an aryl group, it is still more preferable that $R^3$ represents a hydrogen atom and $R^5$ and $R^6$ each independently represent an alkyl group, and it is particularly preferable that $R^3$ represents a hydrogen atom, $R^5$ and $R^6$ each independently represent an alkyl group, and $R^5$ and $R^6$ are bonded to each other to form a ring and condense with a pyrrole ring, thereby forming an indole ring with the pyrrole ring. That is, it is particularly preferable that the specific coloring agent has a structure represented by Formula 1-1.

Formula 1-1

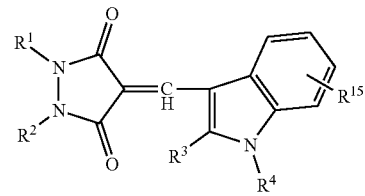

$R^1$ to $R^4$ in Formula 1-1 are synonymous with $R^1$ to $R^4$ in Formula 1, and preferred aspects thereof are also the same.

$R^{15}$ represents a substituent. Examples of the substituent represented by $R^{15}$ include substituents included in the above-described substituent group A. As $R^{15}$, an alkyl group, an aryl group, a halogen atom, an acyl group, or an alkoxycarbonyl group is preferable.

The alkyl group and aryl group in $R^{15}$ are synonymous with the alkyl group and aryl group in $R^3$, $R^5$ and $R^6$, respectively, and preferred aspects thereof are also the same.

Examples of the halogen atom in $R^{15}$ include a chlorine atom, a bromine atom, and an iodine atom.

Examples of the acyl group in $R^{15}$ include an acetyl group, a propionyl group, and a butyroyl group.

As the alkoxycarbonyl group in $R^{15}$, an alkoxycarbonyl group having 2 to 5 carbon atoms is preferable, and examples thereof include a methoxycarbonyl group, an ethoxycarbonyl group, a normal propoxycarbonyl group, and an isopropoxycarbonyl group.

Specific examples of the coloring agent represented by Formula 1 (that is, the specific coloring agent) are shown below.

However, the present disclosure is not limited to these specific examples. "Me" in the specific examples indicates a "methyl group".

D-1
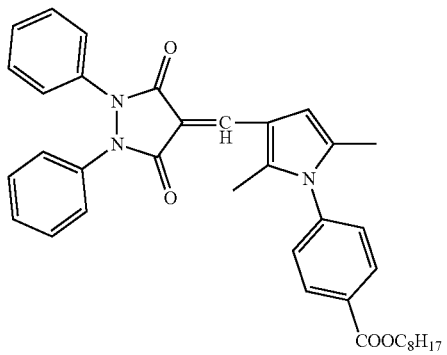
D-2
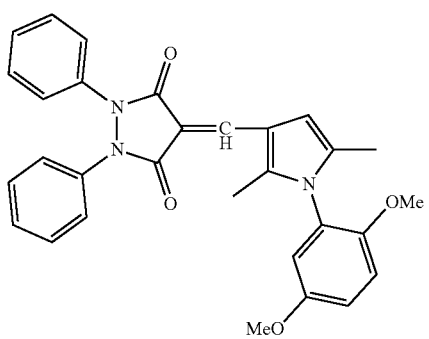
D-3
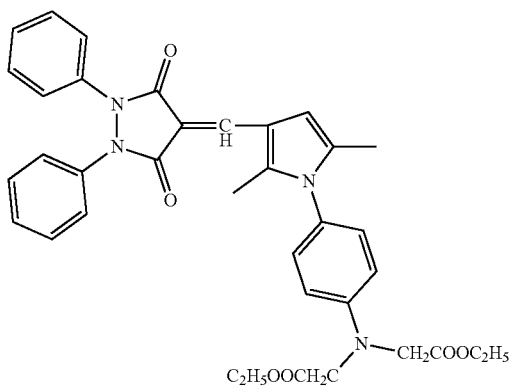
D-4
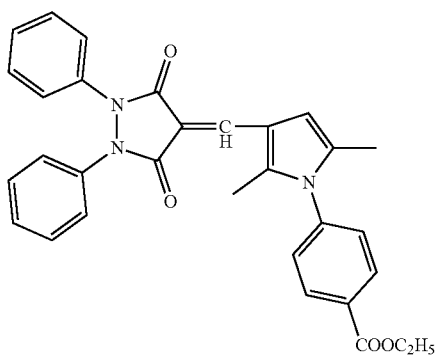
D-5
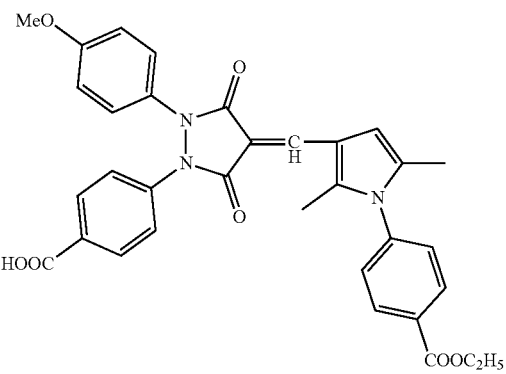
D-6
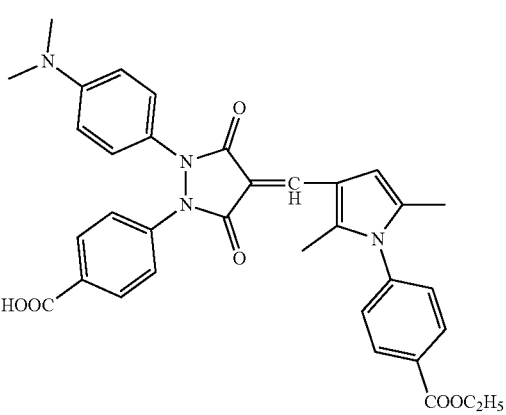
D-7
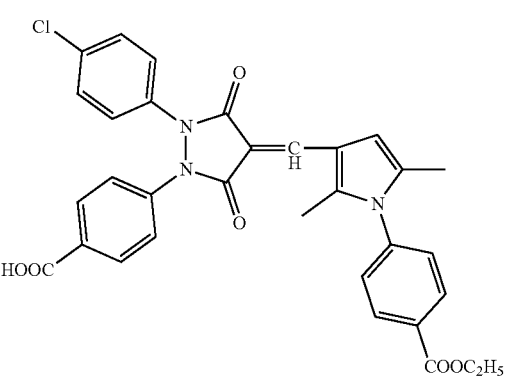
D-8
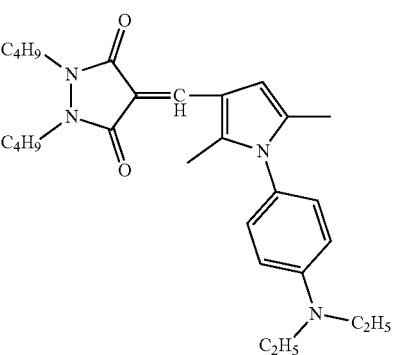

D-9
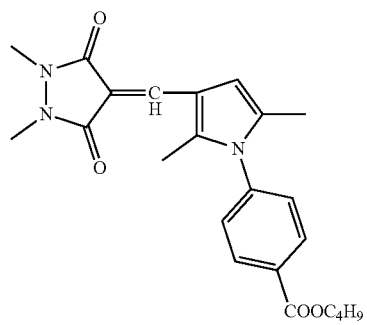
D-10
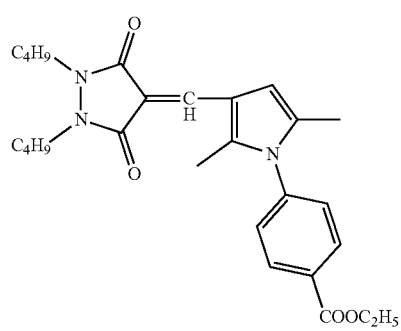
D-11
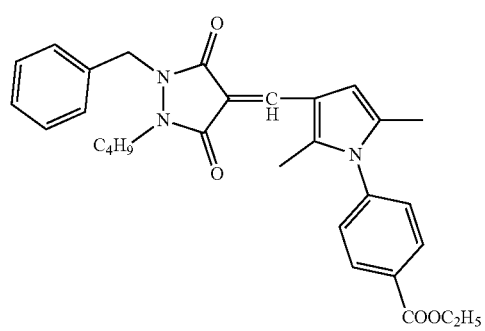
D-12
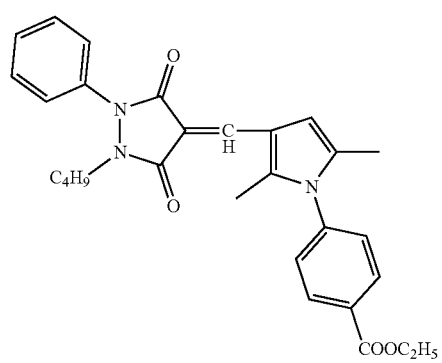
D-13
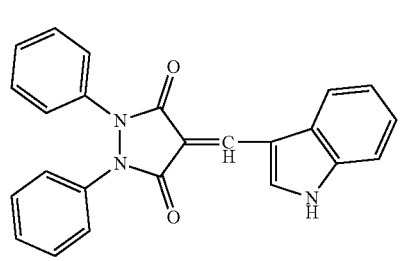
D-14
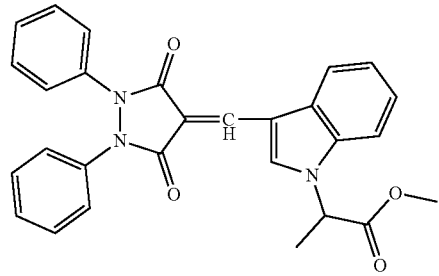
D-15
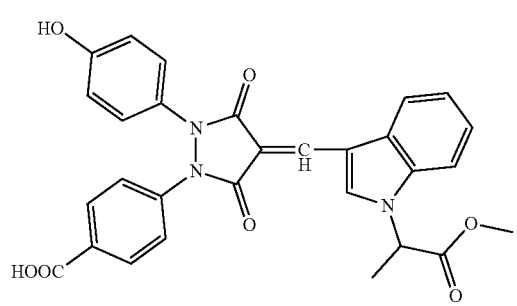
D-16
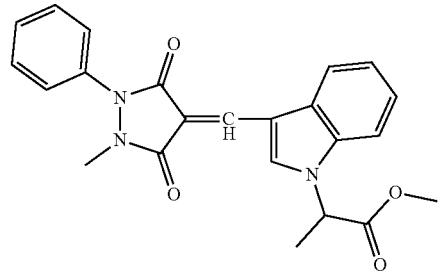
D-17
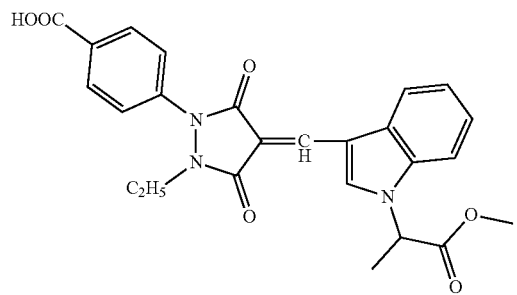
D-18
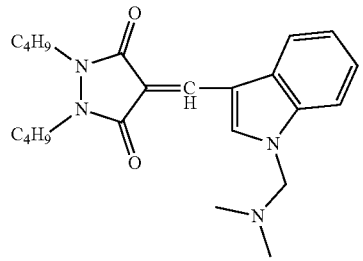

D-19
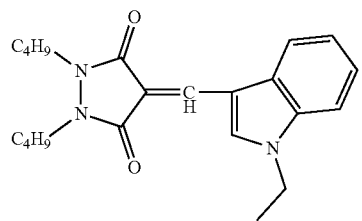
D-20
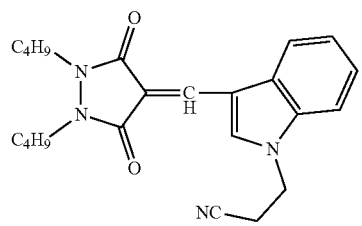
D-21
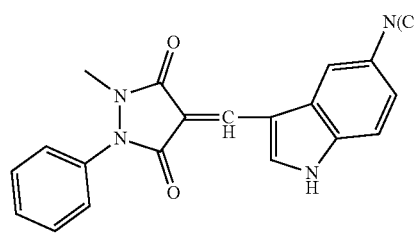
D-22
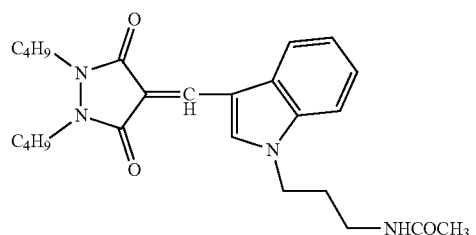
D-23
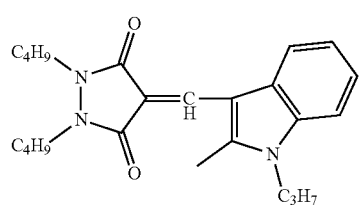
D-24
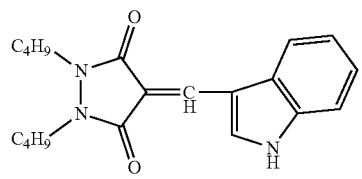
D-25
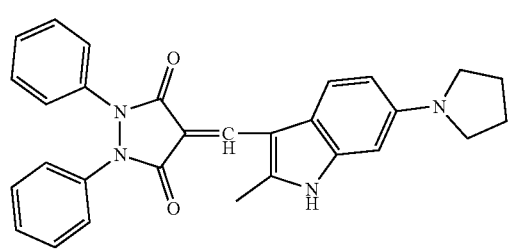
D-26
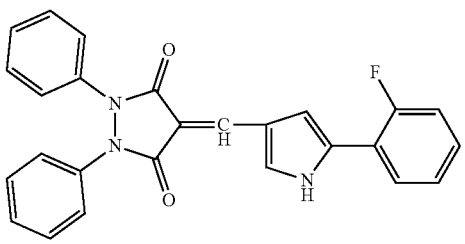
D-27
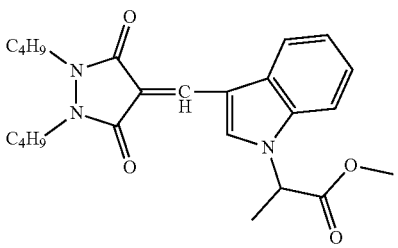
D-28
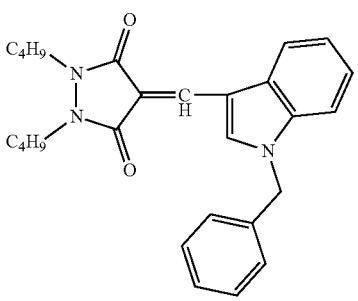
D-29
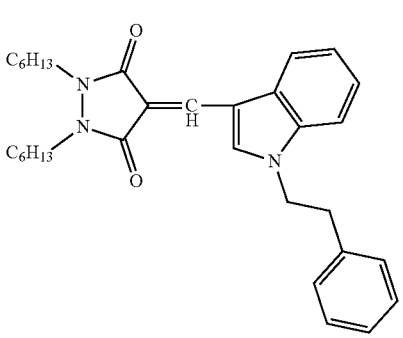
D-30
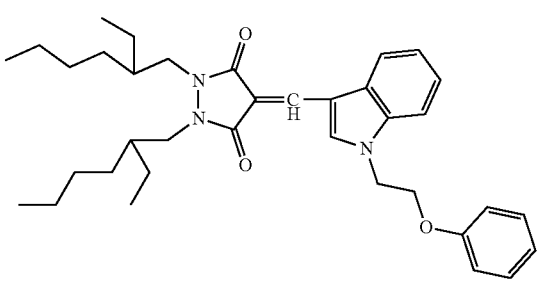

D-31
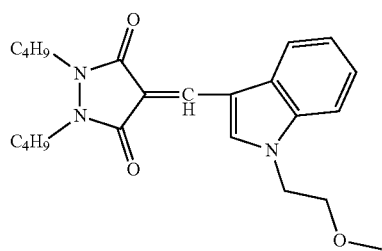
D-32
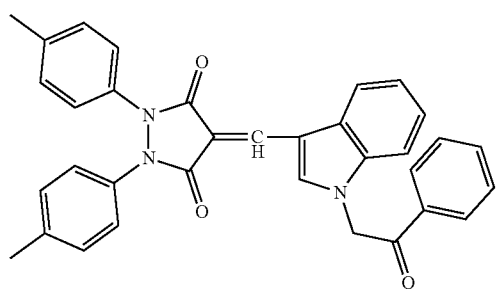
D-33
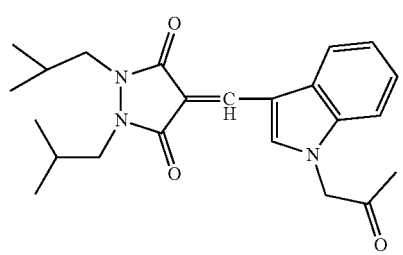
D-34
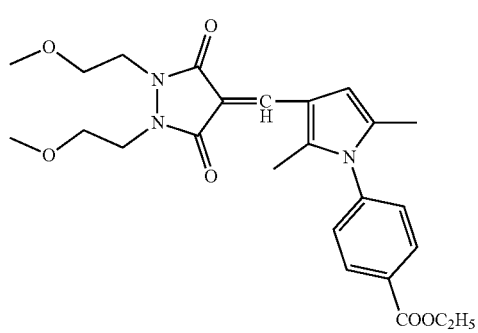
D-35
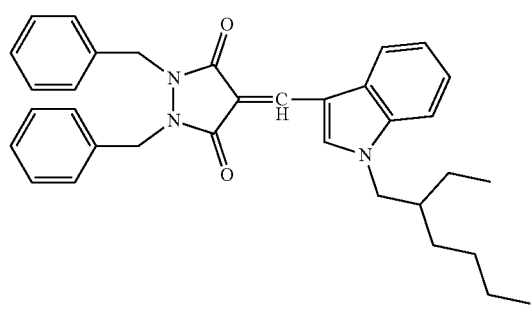
D-36
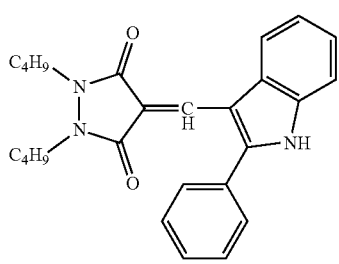
D-37
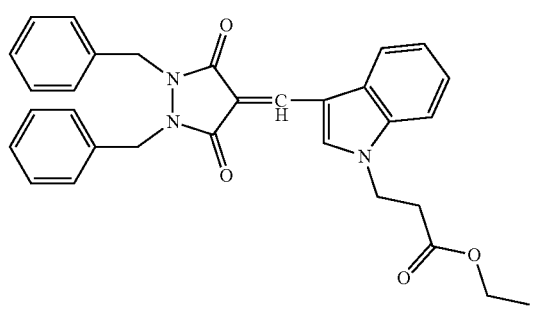
D-38
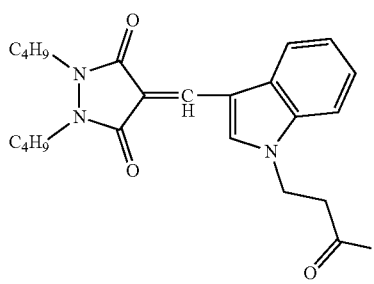
D-39
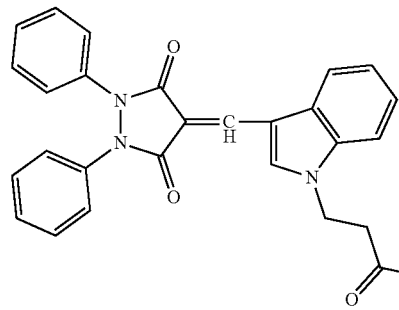
~Synthesis~
The coloring agent represented by Formula 1 (specific coloring agent) can be synthesized by, as described in the following scheme, mixing pyrazolidinedione represented by Formula 3 and an aldehyde represented by Formula 4 in an organic solvent under the

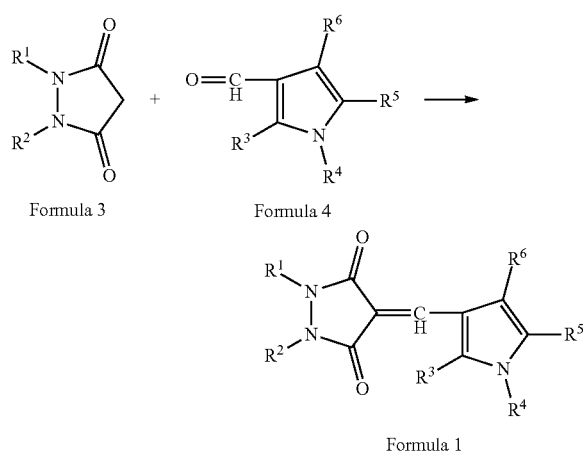

Formula 3    Formula 4

Formula 1

As the organic solvent, for example, alcohol (for example, methanol and ethanol), acetonitrile, N,N-dimethylformamide (DMF), pyridine, acetic acid, or acetic acid anhydride can be used.

A catalyst may be added during the synthesis.

As the catalyst, for example, piperidine, glycine, β-alanine, p-toluenesulfonic acid, or ammonium acetate can be used.

After refluxing, the mixture may be cooled to room temperature (that is, 25° C.) to precipitate.

Further, the precipitated solid may be collected by filtration and then washed with an organic solvent. For the washing, the same organic solvent as the above-described organic solvent used for the synthesis can be used.

The resin composition according to the embodiment of the present disclosure may include the coloring agent represented by Formula 1 (that is, the specific coloring agent) alone or in combination of two or more kinds thereof.

The content of the coloring agent represented by Formula 1 (that is, the specific coloring agent) in the resin composition according to the embodiment of the present disclosure is preferably 0.01% by mass to 5% by mass and more preferably 0.1% by mass to 2% by mass with respect to the total solid content of the resin composition.

Since the coloring agent represented by Formula 1 (that is, the specific coloring agent) has high absorbance especially in a wavelength range of 350 nm to 450 nm, in a case where the content of the specific coloring agent in the resin composition according to the embodiment of the present disclosure is within the above-described range, the resin composition according to the embodiment of the present disclosure is a resin composition having an excellent function of blocking or suppressing wavelength light of 350 nm to 450 nm. The specific coloring agent can block or suppress, for example, ultraviolet rays and blue light well.

(Resin)

The resin composition according to the embodiment of the present disclosure contains at least one resin.

The resin can be appropriately selected from resins which satisfy various physical properties such as transparency, refractive index, and workability, which are required according to the intended use or purpose.

The resin may be a thermoplastic resin or a thermosetting resin.

Examples of the resin include a (meth)acrylic resin, an epoxy resin, an ene-thiol resin, a carbonate resin, an ether resin, an arylate resin, a sulfone resin, an ethersulfone resin, a phenylene resin, an arylene ether phosphine oxide resin, an imide resin, an amide imide resin, an olefin resin, a cyclic olefin resin, an ester resin, a styrene resin, a urethane resin, a cellulose acylate resin, and an episulfide resin.

Examples of the (meth)acrylic resin include polymers including a constitutional unit derived from (meth)acrylic acid and/or an ester thereof. Specific examples thereof include polymers obtained by polymerizing at least one compound selected from the group consisting of (meth)acrylic acid, (meth)acrylic acid ester, (meth)acrylamide, and (meth)acrylonitrile.

Examples of the ester resin include polymers obtained by reacting a polyol (such as ethylene glycol, propylene glycol, glycerin, and trimethylolpropane) with a polybasic acid (such as aromatic dicarboxylic acid (for example, terephthalic acid, isophthalic acid, naphthalenedicarboxylic acid, and dicarboxylic acid in which a hydrogen atom of these aromatic rings is replaced with a methyl group, an ethyl group, or a phenyl group), aliphatic dicarboxylic acid having 2 to 20 carbon atoms (for example, adipic acid, sebacic acid, and dodecanedicarboxylic acid), and alicyclic dicarboxylic acid (for example, cyclohexanedicarboxylic acid)); and polymers obtained by ring-opening polymerization of a cyclic ester compound such as caprolactone monomers (for example, polycaprolactone).

Examples of the epoxy resin include bisphenol A-type epoxy resin, bisphenol F-type epoxy resin, phenol novolac-type epoxy resin, cresol novolac-type epoxy resin, and aliphatic epoxy resin. As the epoxy resin, a commercially available product on the market may be used, and examples of the commercially available product include the following.

Examples of a commercially available product of the bisphenol A-type epoxy resin include jER825, jER827, jER828, jER834, jER1001, jER1002, jER1003, jER1055, jER1007, jER1009, and jER1010 (all manufactured by Mitsubishi Chemical Corporation); and EPICLON 860, EPICLON 1050, EPICLON 1051, and EPICLON 1055 (all manufactured by DIC Corporation).

Examples of a commercially available product of the bisphenol F-type epoxy resin include jER806, jER807, jER4004, jER4005, jER4007, and jER4010 (all manufactured by Mitsubishi Chemical Corporation); EPICLON 830 and EPICLON 835 (both manufactured by DIC Corporation); and LCE-21 and RE-602S (both manufactured by Nippon Kayaku Co., Ltd.).

Examples of a commercially available product of the phenol novolac-type epoxy resin include jER152, jER154, jER157S70, and jER157S65 (all manufactured by Mitsubishi Chemical Corporation); and EPICLON N-740, EPICLON N-770, and EPICLON N-775 (all manufactured by DIC Corporation).

Examples of a commercially available product of the cresol novolac-type epoxy resin include EPICLON N-660, EPICLON N-665, EPICLON N-670, EPICLON N-673, EPICLON N-680, EPICLON N-690, and EPICLON N-695 (all manufactured by DIC Corporation); and EOCN-1020 (manufactured by Nippon Kayaku Co., Ltd.).

Examples of a commercially available product of the aliphatic epoxy resin include ADEKA RESIN EP series (for example, EP-40805, EP-40855, and EP-40885; manufactured by ADEKA Corporation); CELLOXIDE 2021P, CELLOXIDE 2081, CELLOXIDE 2083, CELLOXIDE 2085, EHPE 3150, EPOLEAD PB 3600, and EPOLEAD PB 4700 (all manufactured by Daicel Corporation); DENACOL EX-212L, EX-214L, EX-216L, EX-321L, and EX-850L (all manufactured by Nagase ChemteX Corporation); ADEKA RESIN EP series (for example, EP-4000S, EP-4003S, EP-4010S, and EP-4011S; manufactured by ADEKA Corporation); NC-2000, NC-3000, NC-7300, XD-1000, EPPN-501, and EPPN-502 (all manufactured by ADEKA Corporation); and jER1031S (manufactured by Mitsubishi Chemical Corporation).

Other examples of a commercially available product of the epoxy resin include MARPROOF G-0150M, G-0105SA, G-0130SP, G-0250SP, G-1005S, G-1005SA, G-1010S, G-2050M, G-01100, and G-01758 (all manufactured by NOF Corporation, epoxy group-containing polymer).

The resin may have an acid group.

Examples of the acid group include a carboxy group, a phosphoric acid group, a sulfonic acid group, and a phenolic hydroxy group. The acid group may be only one type or two or more kinds.

The resin having an acid group can be used as an alkali-soluble resin or as a dispersant.

The resin having an acid group is preferably a polymer having a carboxy group in the side chain.

Specific examples of the resin having an acid group include methacrylic acid copolymers, acrylic acid copolymers, itaconic acid copolymers, crotonic acid copolymers, maleic acid copolymers, partially esterified maleic acid copolymers, alkali-soluble phenol resins such as novolak resin, acidic cellulose derivatives having a carboxy group in the side chain, and resins in which an acid anhydride is added to a polymer having a hydroxy group.

In particular, among the resins having an acid group, a copolymer of a (meth)acrylic acid and other monomers copolymerizable with the (meth)acrylic acid is suitable as the alkali-soluble resin.

Examples of the other monomers copolymerizable with the (meth)acrylic acid include alkyl (meth)acrylate, aryl (meth)acrylate, and a vinyl compound.

Examples of the alkyl (meth)acrylate and the aryl (meth) acrylate include methyl (meth)acrylate, ethyl (meth)acrylate, propyl (meth)acrylate, butyl (meth)acrylate, isobutyl (meth)acrylate, pentyl (meth)acrylate, hexyl (meth)acrylate, octyl (meth)acrylate, phenyl (meth)acrylate, benzyl (meth) acrylate, tolyl (meth)acrylate, naphthyl (meth)acrylate, and cyclohexyl (meth)acrylate.

In addition, as the other monomers copolymerizable with the (meth)acrylic acid, N-position-substituted maleimide monomers described in JP1998-300922A (JP-H10-300922A) (for example, N-phenylmaleimide and N-cyclohexylmaleimide), and the like can be used.

Examples of the vinyl compound include styrene, α-methylstyrene, vinyltoluene, glycidyl methacrylate, acrylonitrile, vinyl acetate, N-vinylpyrrolidone, tetrahydrofurfuryl methacrylate, a polystyrene macromonomer, and a polymethyl methacrylate macromonomer.

The other monomers copolymerizable with the (meth) acrylic acid may be used alone or in combination of two or more kinds thereof.

Examples of the resin having an acid group include a benzyl (meth)acrylate/(meth)acrylic acid copolymer, a benzyl (meth)acrylate/(meth)acrylic acid/2-hydroxyethyl (meth)acrylate copolymer, a benzyl (meth)acrylate/(meth) acrylic acid/other monomer copolymer, and a 2-hydroxyethyl (meth)acrylate polymer; and a 2-hydroxypropyl (meth) acrylate/polystyrene macromonomer/benzyl methacrylate/ methacrylic acid copolymer, a 2-hydroxy-3-phenoxypropylacrylate/polymethyl methacrylate macromonomer/benzyl methacrylate/methacrylic acid copolymer, a 2-hydroxyethyl methacrylate/polystyrene macromonomer/methyl methacrylate/methacrylic acid copolymer, and a 2-hydroxyethyl methacrylate/polystyrene macromonomer/benzyl methacrylate/methacrylic acid copolymer, which are described in JP1995-140654A (JP-H07-140654A).

As the resin having an acid group, reference can be made to the description in paragraphs 0558 to 0571 of JP2012-208494A (paragraphs 0685 to 0700 of the corresponding US2012/0235099A) and the description in paragraphs 0076 to 0099 of JP2012-198408A, the contents of which are incorporated herein by reference. In addition, as the resin having an acid group, ACRYBASE FF-426 (manufactured by NIPPON SHOKUBAI CO., LTD.) can also be used.

The acid value of the resin having an acid group is preferably 30 mgKOH/g to 200 mgKOH/g. The lower limit or the acid value is more preferably 50 mgKOH/g or more and still more preferably 70 mgKOH/g or more. In addition, the upper limit of the acid value is more preferably 150 mgKOH/g or less and still more preferably 120 mgKOH/g or less.

The acid value of the resin is a value calculated by measuring in accordance with JIS K0070: 1992 and converting as 1 mmol/g=56.1 mgKOH/g.

The resin may have a curable group.

The resin is preferably a copolymer including a constitutional unit having a curable group.

Examples of the curable group include a group having an ethylenically unsaturated bond, an epoxy group, a methylol group, and an alkoxysilyl group.

Examples of the group having an ethylenically unsaturated bond include a vinyl group, a (meth)allyl group, and a (meth)acryloyl group.

Examples of the alkoxysilyl group include a monoalkoxysilyl group, a dialkoxysilyl group, and a trialkoxysilyl group.

Examples of the constitutional unit having a curable group include constitutional units represented by Formulae (A2-1) to (A2-4).

(A2-1)

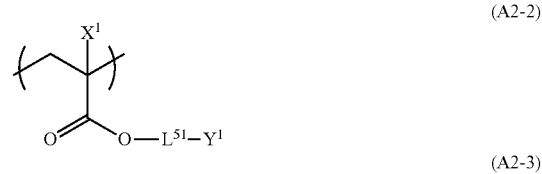

(A2-2)

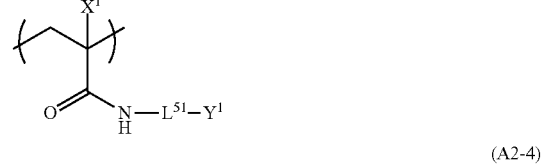

(A2-3)

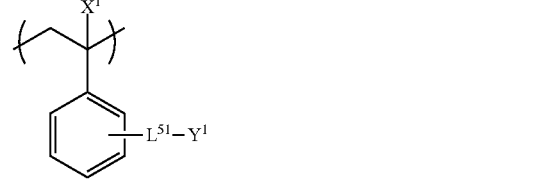

(A2-4)

$X^1$ represents a hydrogen atom or an alkyl group.

The number of carbon atoms in the alkyl group of $X^1$ is preferably 1 to 5, more preferably 1 to 3, and still more preferably 1.

$X^1$ is preferably a hydrogen atom or a methyl group.

$L^{51}$ represents a single bond or a divalent linking group.

Examples of the divalent linking group in $L^{51}$ include an alkylene group, an arylene group, —O—, —S—, —CO—, —COO—, —OCO—, —SO$_2$—, —NR— (R represents a hydrogen atom or an alkyl group, and is preferably a hydrogen atom), and a group in which two or more of these are combined.

As the divalent linking group in $L^{51}$, a group in which at least one selected from an alkylene group and an arylene group is combined with —O— is preferable.

The number of carbon atoms in the alkylene group of $L^{51}$ is preferably 1 to 30, more preferably 1 to 15, and still more preferably 1 to 10. The alkylene group may be unsubstituted or has a substituent, but is preferably unsubstituted. The alkylene group may be linear, branched, or cyclic. In addition, the cyclic alkylene group may be monocyclic or polycyclic.

The number of carbon atoms in the arylene group of $L^{51}$ is preferably 6 to 18, more preferably 6 to 14, and still more preferably 6 to 10.

$Y^1$ represents a curable group.

Examples of the curable group include a group having an ethylenically unsaturated bond, an epoxy group, a methylol group, and an alkoxysilyl group. Details of the group having an ethylenically unsaturated bond, the epoxy group, the methylol group, and the alkoxysilyl group are as described above.

As the resin containing a curable group, a commercially available product on the market may be used. Examples of the commercially available product of the resin containing a curable group include Dianal BR Series (polymethyl methacrylate (PMMA), for example Dianal BR-80, BR-83, and BR-87, manufactured by Mitsubishi Rayon Co., Ltd.); Photomer 6173 (COOH-containing polyurethane acrylic oligomer, Diamond Shamrock Co., Ltd.); Viscoat R-264 and KS Resist 106 (both manufactured by Osaka Organic Chemical Industry Ltd.); Cyclomer P series (for example, ACA230AA) and Placcel CF 200 series (all manufactured by Daicel Corporation); Ebecryl 3800 (manufactured by Daicel UCB Company, Ltd.); and Acrycure RD-F8 (manufactured by Nippon Shokubai Co., Ltd.). In addition, examples thereof also include the above-described commercially available products of the epoxy resin.

For example, in a case where the resin composition according to the embodiment of the present disclosure is used for a lens (for example, a spectacle lens), as the resin, a thermoplastic resin such as a carbonate resin and a (meth)acrylic resin (for example, polymethylmethacrylate (PMMA)), and a thermosetting resin such as a urethane resin are suitable.

Examples of a commercially available product of the carbonate resin on the market include a polycarbonate resin composition (trade name: Calibre 200-13, manufactured by Sumitomo Dow Limited) and a diethylene glycol bisallyl carbonate resin (trade name: CR-39, manufactured by PPG Industries, Inc.).

As the urethane resin, a thiourethane resin is preferable. Examples of a commercially available product the thiourethane resin on the market include a thiourethane resin monomer (trade name: MR-7, MR-8, MR-10, and MR-174; manufactured by Mitsui Chemicals, Inc.).

The weight-average molecular weight (Mw) of the resin is preferably 2,000 to 2,000,000.

The lower limit of Mw of the resin is more preferably 5,000 or more, still more preferably 10,000 or more, and particularly preferably 50,000 or more. The upper limit of Mw of the resin is more preferably 1,000,000 or less, still more preferably 500,000 or less, and particularly preferably 200,000 or less.

In addition, in a case of using an epoxy resin, the weight-average molecular weight (Mw) of the epoxy resin is preferably 100 or more, and more preferably 200 to 2,000,000. The upper limit of Mw of the epoxy resin is still more preferably 1,000,000 or less and particularly preferably 500,000 or less. The lower limit of Mw of the epoxy resin is more preferably 2000 or more.

The weight-average molecular weight (Mw) is a value measured by gel permeation chromatography (GPC).

In the measurement by GPC, HLC (registered trademark)-8020GPC (manufactured by Tosoh Corporation) is used as a measuring device, three columns of TSKgel (registered trademark) Super Multipore HZ-H (4.6 mmID×15 cm, manufactured by Tosoh Corporation) are used as a column, and tetrahydrofuran (THF) is used as an eluent. In addition, as the measurement conditions, a sample concentration of 0.45% by mass, a flow rate of 0.35 ml/min, a sample injection amount of 10 µl, and a measurement temperature of 40° C. are set, and a RI detector is used.

The calibration curve is created from eight samples of "Standard sample TSK standard, polystyrene" manufactured by Tosoh Corporation: "F-40", "F-20", "F-4", "F-1", "A-5000", "A-2500", "A-1000", and "n-propylbenzene".

The resin composition according to the embodiment of the present disclosure may include the resin alone or in combination of two or more kinds thereof.

The content of the resin in the resin composition according to the embodiment of the present disclosure is preferably 70% by mass to 99.9% by mass and more preferably 80% by mass to 99.9% by mass with respect to the total solid content of the resin composition.

In a case where the content of the resin in the resin composition according to the embodiment of the present disclosure is within the above-described range, moldability during molding is good.

(Coloring Agent Other than Specific Coloring Agent)

The resin composition according to the embodiment of the present disclosure may include a coloring agent (for example, a dye and a pigment) other than the above-described specific coloring agent as necessary, depending on the intended use or purpose.

Examples of the dye other than the specific coloring agent include phthalocyanine dyes, xanthene dyes, triarylmethane dyes, methine dyes, azo dyes, and anthraquinone dyes, which are described as phthalocyanine compounds in US2008/0076044A1; and dipyrromethene dyes described in JP2008-292970A.

The dye other than the specific coloring agent may or may not have a maximal absorption wavelength in a wavelength range of 450 nm to 500 nm.

As the dye other than the specific coloring agent, from the viewpoint of better expressing the blocking function and suppressing function of ultraviolet rays and blue light, phthalocyanine dyes, xanthene dyes, triarylmethane dyes, methine dyes, azo dyes, anthraquinone dyes, dipyrromethene dyes, and the like are suitable.

Examples of the pigment other than the specific coloring agent include perylene, perinone, quinacridone, quinacridonequinone, anthraquinone, anthraquinone, benzimidazolone, disazo condensation, disazo, azo, indanthrone, phthalocyanine, triarylcarbonium, dioxazine, aminoanthraquinone, diketopyrrolopyrrole, indigo, thioindigo, isoindoline, isoindolinone, pyranthrone, and isodibenzanthrone.

In a case where the resin composition according to the embodiment of the present disclosure includes a pigment other than the specific coloring agent, from the viewpoint of visibility in a case of being applied to applications of an optical material, the average primary particle diameter of the pigment is preferably 200 nm or less, more preferably 10 nm to 200 nm, and still more preferably 10 nm to 100 nm.

In a case where the resin composition according to the embodiment of the present disclosure includes a pigment, it is preferable to include the pigment in the resin composition by mixing the pigment with a dispersant, an organic solvent, and the like in advance to prepare a pigment dispersion liquid in which the pigment is dispersed, and mixing with other components.

(Ultraviolet Absorber)

The resin composition according to the embodiment of the present disclosure may include an ultraviolet absorber as necessary.

According to the ultraviolet absorber, the effect of the resin composition according to the embodiment of the present disclosure of blocking or suppressing ultraviolet rays can be further enhanced.

Examples of the ultraviolet absorber include ultraviolet rays-absorbing compounds selected from the group consisting of bentriazole-based compounds, triazine-based compounds, benzophenone-based compounds, merocyanine-based compounds, cyanine-based compounds, dibenzoylmethane-based compounds, cinnamic acid-based compounds, acrylate-based compounds, benzoic acid ester-based compounds, oxalic acid diamide-based compounds, formamidine-based compounds, benzoxazineone-based compounds, benzoxazole-based compounds, and benzodithiol-based compounds. The ultraviolet absorber which can be used in the resin composition according to the embodiment of the present disclosure is described, for example, in "Fine Chemicals" (2004, May) pp. 28 to 38; Toray Research Center Inc., Technical Survey Dept., Ed., "New Trend of Functional Polymer Additives" (Toray Research Center Inc., 1999), pp. 96 to 140; Yasuichi Okatsu Ed., "Development of Polymer Additives and Environmental Measures" (CMC Publishing, 2003), pp. 54 to 64; and Technical Information Association Co., Ltd. "Polymer Deterioration/Discoloration Mechanism and Its Stabilization Technology-Know-how Collection-" (Technical Information Association, 2006), and from compounds described in these documents, the ultraviolet absorber can be appropriately selected depending on the intended purpose.

Examples of the ultraviolet absorber include the following compounds.

Examples of the benzoxazole-based compound include a compound represented by General Formula (II) in JP4311869B, described as a fluorescent whitening agent.

Examples of the benzoxazineone-based compound include compounds described in JP5591453B and JP5250289B.

Examples of the merocyanine-based compound include compounds described in JP2011-184414A.

Examples of the benzodithiol-based compound include compounds described in JP5450994B and JP5364311B.

Specific examples of the benzoxazinone-based compound include UV-1, UV-2, and UV-3 having the following structures.

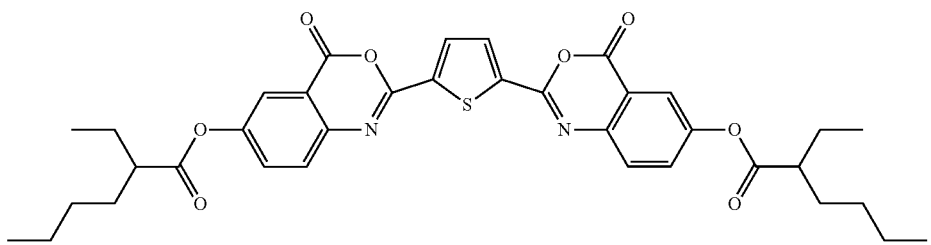

UV-1

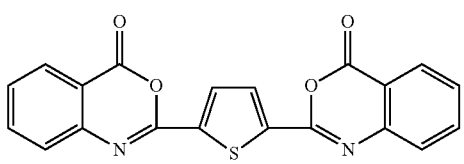

UV-2

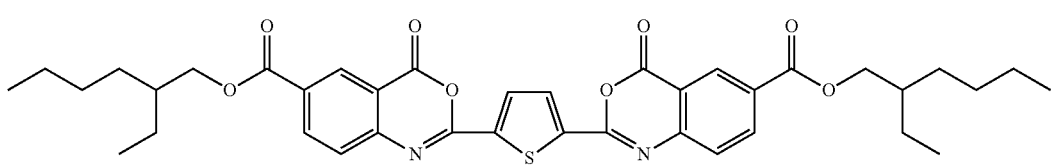

UV-3

Specific examples of the merocyanine-based compound include UV-4 and UV-5 having the following structures.

UV-4
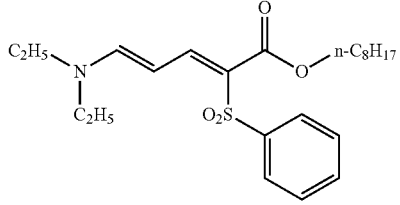

UV-5
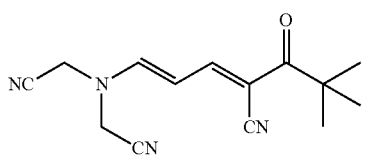

Specific examples of the benzoxazole-based compound include UV-6 and UV-7 having the following structures.

UV-6
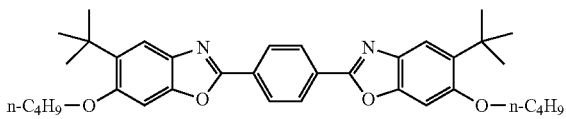

UV-7
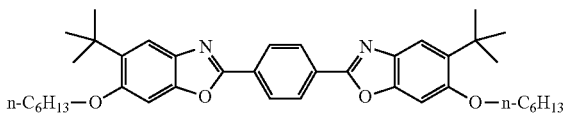

Specific examples of the benzodithiol-based compound include UV-8 and UV-9 having the following structures.

UV-8
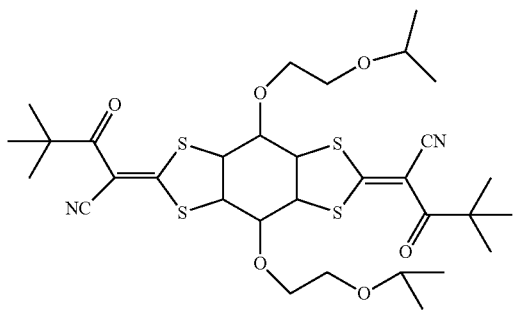

-continued

UV-9
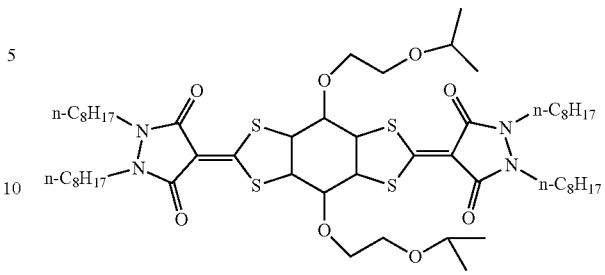

In a case of including an ultraviolet absorber, the resin composition according to the embodiment of the present disclosure may include the ultraviolet absorber alone or in combination of two or more kinds thereof.

In a case where the resin composition according to the embodiment of the present disclosure contains an ultraviolet absorber, the content of the ultraviolet absorber in the resin composition may be appropriately selected depending on the type of the ultraviolet absorber, and may be generally 0.01% by mass to 20% by mass with respect to the total mass of the resin composition.

(Other Components)

The resin composition according to the embodiment of the present disclosure can include a component other than the above-described components (so-called other components).

Examples of the other components include a filler, a surfactant, a polymerizable compound, a polymerization initiator, an adhesion promoter, an antioxidant, an ultraviolet absorber, and an anti-aggregation agent.

As the polymerizable compound and the polymerization initiator, those which can be used in the liquid composition described later can be used in the same manner, and thus the description thereof will be omitted here.

The resin composition according to the embodiment of the present disclosure can be prepared by mixing the coloring agent represented by Formula 1 (that is, the specific coloring agent) and the resin, and as necessary, the ultraviolet absorber and other components.

<Liquid Composition>

A liquid composition according to an embodiment of the present disclosure includes a coloring agent represented by Formula 1 (that is, the specific coloring agent), and a solvent.

Since the liquid composition according to the embodiment of the present disclosure includes the specific coloring agent, blocking property in a wavelength range of at least 350 nm to 450 nm is excellent, and light resistance and heat resistance are also excellent.

The liquid composition according to the embodiment of the present disclosure may further include a coloring agent other than the specific coloring agent, an ultraviolet absorber, and other components, as necessary. Details of the coloring agent other than the specific coloring agent, the ultraviolet absorber, and the other components are the same as in the case of the resin composition according to the embodiment of the present disclosure described above, and thus the description thereof will be omitted here.

(Coloring Agent)

The coloring agent represented by Formula 1 (that is, the specific coloring agent) included in the liquid composition according to the embodiment of the present disclosure is synonymous with the specific coloring agent in the resin composition according to the embodiment of the present disclosure, and preferred aspects thereof are also the same.

In particular, from the viewpoint of light resistance, as $R^1$ and $R^2$ in Formula 1, it is more preferable that $R^1$ is an alkyl group, and it is more preferable that $R^1$ represents an alkyl group and $R^2$ represents an alkyl group or an aryl group. For the same reason, it is still more preferable that both $R^1$ and $R^2$ independently represent an alkyl group.

In addition, from the viewpoint of heat resistance and light resistance, it is also preferable that both $R^1$ and $R^2$ of $R^1$ and $R^2$ in Formula 1 are aryl groups. It is preferable that, in a case where $R^1$ and $R^2$ each independently represent an aryl group, $R^3$, $R^5$, and $R^6$ each independently represent a hydrogen atom, an alkyl group, or an aryl group and at least one of $R^3$ or $R^6$ represents a hydrogen atom.

The liquid composition according to the embodiment of the present disclosure may include the coloring agent represented by Formula 1 (the specific coloring agent) alone or in combination of two or more kinds thereof.

The content of the coloring agent represented by Formula 1 (the specific coloring agent) in the liquid composition according to the embodiment of the present disclosure is preferably 0.01% by mass to 20% by mass and more preferably 0.1% by mass to 5% by mass with respect to the total solid content of the liquid composition.

Since the coloring agent represented by Formula 1 (the specific coloring agent) has high absorbance especially in a wavelength range of 350 nm to 450 nm, in a case where the content of the specific coloring agent in the liquid composition according to the embodiment of the present disclosure is within the above-described range, the liquid composition according to the embodiment of the present disclosure is a liquid composition having an excellent function of blocking or suppressing wavelength light of 350 nm to 450 nm.

(Solvent)

The liquid composition according to the embodiment of the present disclosure contains at least one solvent.

Examples of the solvent include water, an organic solvent, and a mixed solvent of water and an organic solvent.

As the water, distilled water, ion exchange water, or the like can be used.

The organic solvent can be appropriately selected depending on the intended use or purpose of the liquid composition. Examples of the organic solvent include esters, ethers, ketones, and aromatic hydrocarbons.

Examples of the ester include ethyl acetate, n-butyl acetate, isobutyl acetate, amyl formate, isoamyl acetate, butyl propionate, isopropyl butyrate, ethyl butyrate, butyl butyrate, methyl lactate, ethyl lactate, oxyacetic acid alkyl ester solvents (for example, methyl oxyacetate, ethyl oxyacetate, butyl oxyacetate (specific examples thereof include methyl methoxyacetate, ethyl methoxyacetate, butyl methoxyacetate, methyl ethoxyacetate, and ethyl ethoxyacetate)), 3-oxypropionic acid alkyl ester solvents (for example, methyl 3-oxypropionate and ethyl 3-oxypropionate (specific examples thereof include methyl 3-methoxypropionate, ethyl 3-methoxypropionate, methyl 3-ethoxypropionate, and ethyl 3-ethoxypropionate)), 2-oxypropionic acid alkyl ester solvents (for example, methyl 2-oxypropionate, ethyl 2-oxypropionate, and propyl 2-oxypropionate (specific examples thereof include methyl 2-methoxypropionate, ethyl 2-methoxypropionate, propyl 2-methoxypropionate, methyl 2-ethoxypropionate, and ethyl 2-ethoxypropionate)), 2-oxy-2-methylpropionic acid alkyl ester solvents (methyl 2-oxy-2-methylpropionate and ethyl 2-oxy-2-methylpropionate (specific examples thereof include methyl 2-methoxy-2-methylpropionate and 2-ethoxy-2-methylpropionate), methyl pyruvate, ethyl pyruvate, propyl pyruvate, methyl acetoacetate, ethyl acetoacetate, methyl 2-oxobutate, ethyl 2-oxobutate, cyclohexyl acetate, and 1-methyl-2-methoxyethyl propionate.

Examples of the ether include diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate (also referred to as PEGMEA), diethylene glycol monoethyl ether acetate (also referred to as ethyl carbitol acetate), diethylene glycol monobutyl ether acetate (also referred to as butyl carbitol acetate), propylene glycol monoethyl ether acetate, and propylene glycol monopropyl ether acetate.

Examples of the ketone include methyl ethyl ketone, cyclohexanone, 2-heptanone, and 3-heptanone.

Suitable examples of the aromatic hydrocarbon include toluene and xylene.

The liquid composition according to the embodiment of the present disclosure may include the organic solvent alone, or from the viewpoint of application, or improving solubility of each component or shape of the coating surface, may include the organic solvent in combination of two or more kinds thereof.

In a case where the liquid composition according to the embodiment of the present disclosure includes two or more kinds of organic solvents, it is preferable to include two or more kinds selected from the group consisting of methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol monomethyl ether acetate.

The content of the solvent in the liquid composition according to the embodiment of the present disclosure is preferably an amount such that the total solid content in the liquid composition is 10% by mass to 80% by mass, and more preferably an amount such that the total solid content in the liquid composition is 15% by mass to 60% by mass.

The liquid composition according to the embodiment of the present disclosure can be used as a composition having curing properties (so-called curable composition).

The curable composition is a composition which can be cured by applying energy.

The curable composition is preferably a composition which exhibits curing properties by, for example, irradiation with, as energy, visible light, ultraviolet rays (UV), electron beam, and the like, or by heating. Among these, as the curable composition, from the viewpoint of general-purpose properties, good curing sensitivity, and the like, a composition which exhibits curing properties by irradiation with ultraviolet rays is more preferable.

(Polymerizable Compound)

The liquid composition according to the embodiment of the present disclosure can be prepared as a composition having curing properties by further including a polymerizable compound in addition to the components described above. As the polymerizable compound, a compound which can be polymerized and cured by applying energy can be used without limitation.

Examples of the polymerizable compound include an addition-polymerizable compound having at least one ethylenically unsaturated double bond.

The addition-polymerizable compound can be selected from compounds having at least one ethylenically unsaturated bond at the terminal, and a compound having two or more ethylenically unsaturated bonds at the terminal is preferable.

The polymerizable compound is, for example, any of a monomer, a prepolymer (that is, a dimer, a trimer, or an oligomer), a mixture thereof, or a polymer of a compound selected from monomers and prepolymers.

Examples of the polymerizable compound include unsaturated carboxylic acids (for example, acrylic acid, methacrylic acid, itaconic acid, crotonic acid, isocrotonic acid, and maleic acid), esters of unsaturated carboxylic acid, amides of unsaturated carboxylic acid, and polymers of unsaturated carboxylic acid, or an ester or amide thereof. Among these, as the polymerizable compound, an ester of unsaturated carboxylic acid and aliphatic polyhydric alcohol, an amide of unsaturated carboxylic acid and aliphatic polyvalent amine, or a homopolymer or copolymer thereof is preferable.

In addition, examples of the polymerizable compound include an addition reactant of an unsaturated carboxylic acid ester or unsaturated carboxylic acid amide having a nucleophilic substituent (for example, a hydroxy group, an amino group, and a mercapto group) and a monofunctional or polyfunctional isocyanate compound or epoxy compound; a dehydration condensation reactant of an unsaturated carboxylic acid ester or unsaturated carboxylic acid amide having a nucleophilic substituent and a monofunctional or polyfunctional carboxylic acid; an addition reactant of an unsaturated carboxylic acid ester or unsaturated carboxylic acid amide having an electrophilic substituent (for example, isocyanate group and epoxy group) and a monofunctional or polyfunctional alcohol, amine, or thiol; and a substitution reactant of an unsaturated carboxylic acid ester or unsaturated carboxylic acid amide having a leaving substituent (for example, a halogen group and a tosyloxy group) and a monofunctional or polyfunctional alcohol, amine, or thiol. Further, examples of the polymerizable compound also include a compound obtained by replacing the above-described unsaturated carboxylic acid with an unsaturated phosphonic acid, styrene, or vinyl ether.

In a case where the liquid composition according to the embodiment of the present disclosure includes a polymerizable compound, details such as the structure of the polymerizable compound, selection of single use or combined use of two or more kinds, and content may be optionally set according to the intended use or purpose of the liquid composition.

For example, from the viewpoint of curing sensitivity of the liquid composition, as the polymerizable compound, a compound having a high content of a group having an ethylenically unsaturated double bond (also referred to as an unsaturated group) per one molecule is preferable, and a bi- or higher functional compound having two or more unsaturated groups is more preferable. In addition, for example, from the viewpoint of increasing the strength of the resin layer formed by applying the liquid composition, or the like, as the polymerizable compound, a tri- or higher functional compound having 3 or more unsaturated groups (for example, a hexafunctional acrylate compound) is preferable.

In addition, in the liquid composition according to the embodiment of the present disclosure, as the polymerizable compound, a plurality of compounds having different functional numbers or a plurality of compounds having different types of polymerizable groups (for example, acrylic acid ester, methacrylic acid ester, styrene compound, and vinyl ether compound) may be used in combination. By using the plurality of polymerizable compounds in combination, it is possible to adjust both the sensitivity and the strength.

As the polymerizable compound, a commercially available product on the market may be used. Examples of the commercially available product of the polymerizable compound include KYARAD (registered trademark) PET-30 and KYARAD (registered trademark) TPA-330 of Nippon Kayaku Co., Ltd., POLYVEST (registered trademark) 110M of EVONIK, and Polyfunctional acrylate A-9300 (trade name) of Shin Nakamura Chemical Industry Co., Ltd.

In a case of including a polymerizable compound, the liquid composition according to the embodiment of the present disclosure may include the polymerizable compound alone or in combination of two or more kinds thereof.

The content of the polymerizable compound in the liquid composition according to the embodiment of the present disclosure is not particularly limited.

In a case where the liquid composition according to the embodiment of the present disclosure includes the polymerizable compound, the content of the polymerizable compound in the liquid composition is preferably 30% by mass to 99.5% by mass, more preferably 50% by mass to 99% by mass, and still more preferably 60% by mass to 98% by mass with respect to the total solid content of the liquid composition.

In the liquid composition according to the embodiment of the present disclosure, a polymer compound can be used as the polymerizable compound.

Examples of the polymerizable polymer compound include a (meth)acrylic resin, an ester resin, a urethane resin, and a fluororesin.

As the polymerizable polymer compound, a commercially available product on the market may be used. Examples of the commercially available product of the polymerizable polymer compound include Dianal BR Series (polymethyl methacrylate (PMMA), for example Dianal BR-80, BR-83, and BR-87, manufactured by Mitsubishi Rayon Co., Ltd.); Photomer 6173 (COOH-containing polyurethane acrylic oligomer, Diamond Shamrock Co., Ltd.); Viscoat R-264 and KS Resist 106 (both manufactured by Osaka Organic Chemical Industry Ltd.); Cyclomer P series (for example, ACA230AA) and Placcel CF 200 series (all manufactured by Daicel Corporation); Ebecryl 3800 (manufactured by Daicel UCB Company, Ltd.); and Acrycure RD-F8 (manufactured by Nippon Shokubai Co., Ltd.).

In a case of including a polymerizable polymer compound, the liquid composition according to the embodiment of the present disclosure may include the polymerizable polymer compound alone or in combination of two or more kinds thereof. However, from the viewpoint of film uniformity, it is preferable to include one kind alone.

From the viewpoint of improving the strength after curing, the polymerizable polymer compound is preferably a compound capable of forming a crosslinking structure. A method for forming the crosslinking structure is not particularly limited, and examples thereof include a method of using a polymerizable polymer compound in combination with a polyfunctional (meth)acrylate monomer having an unsaturated group which can be additive-polymerized with an unsaturated group of the polymerizable polymer compound, and a method of using a polymerizable polymer compound (for example, a (meth)acrylic resin) into which a reactive group (for example, a hydroxyl group) has been introduced in combination with a crosslinking agent having a crosslinkable group capable of reacting with the reactive group.

Examples of the reactive group include a group including an active hydrogen, and specific examples thereof include a group selected from the group consisting of a hydroxyl group, a primary amino group, and a secondary amino group.

As the polymerizable polymer compound into which the reactive group has been introduced, for example, a (meth) acrylic resin including a structural unit derived from a (meth)acrylate monomer and having two or more groups including an active hydrogen is preferable.

Examples of the crosslinking agent include polyisocyanates having two or more isocyanate groups as the crosslinkable group. As the crosslinking agent, a commercially available product on the market may be used. Examples of the commercially available product of the crosslinking agent include AD-TMP and A-9550 (both are trade names) of Shin Nakamura Chemical Industry Co., Ltd.

Among these, as the method for forming the crosslinking structure, a method of using a (meth)acrylic resin having two or more (preferably three or more groups including an active hydrogen in combination with a crosslinking agent having two or more isocyanate groups (preferably a polyisocyanate having two or more isocyanate groups and more preferably a polyisocyanate having three or more isocyanate groups). In this method, the crosslinking structure can be formed by reacting the group including an active hydrogen with the isocyanate group.

The above-described method is preferable from the viewpoint that the crosslink density in the formed resin body (for example, the resin layer) is further increased and the strength of the resin body is further improved.

In a case where the liquid composition according to the embodiment of the present disclosure includes the polymerizable compound, the content of the polymerizable compound in the liquid composition is preferably 30% by mass to 99.5% by mass, more preferably 50% by mass to 99% by mass, and still more preferably 60% by mass to 98% by mass with respect to the total solid content of the liquid composition.

In addition, in a case of using the polymerizable polymer compound into which the reactive group has been introduced in combination with the crosslinking agent, the content of the crosslinking agent in the liquid composition is preferably 5 parts by mass to 80 parts by mass and more preferably 10 parts by mass to 50 parts by mass with respect to 100 parts by mass of the polymerizable polymer compound.

(Polymerization Initiator)

The liquid composition according to the embodiment of the present disclosure may further include a polymerization initiator in addition to the components described above. In a case where the liquid composition according to the embodiment of the present disclosure further includes a polymerization initiator, the polymerization reaction of the polymerizable compound can be initiated well. As the polymerization initiator, a compound capable of generating initiating species required for the polymerization reaction by applying energy can be used.

The polymerization initiator can be appropriately selected from, for example, a photopolymerization initiator and a thermal polymerization initiator. As the polymerization initiator, a photopolymerization initiator is preferable.

As the photopolymerization initiator, for example, a compound having light absorption from the ultraviolet region to the visible region (for example, 280 nm to 400 nm) is preferable. Examples of such a compound include a photoradical initiator which generates an active radical and initiates photoradical polymerization, and a cation initiator that initiates photocationic polymerization.

Examples of the photopolymerization initiator include halogenated hydrocarbon derivatives such as a photopolymerization initiator having a triazine skeleton and a photopolymerization initiator having an oxadiazole skeleton; acylphosphine compounds such as acylphosphine oxide; hexaaryl biimidazole; oxime compounds such as an oxime derivative; organic peroxides; thio compounds; ketone compounds; aromatic onium salts; ketooxime ethers; aminoacetophenone compounds; and hydroxyacetophenones.

Examples of the aminoacetophenone-based initiator include initiators having an absorption wavelength at 365 nm or 405 nm, which is described in JP2009-191179A, and initiators described in JP1998-291969A (JP-H10-291969A).

In addition, examples of the aminoacetophenone-based initiator include acylphosphine oxide-based initiators described in JP4225898B.

As the photopolymerization initiator, a synthetic product may be used, or a commercially available product on the market may be used.

Examples of the commercially available product of the photopolymerization initiator include hydroxyacetophenone-based initiators such as IRGACURE (registered trademark) 184, DAROCUR (registered trademark) 1173, IRGACURE (registered trademark) 500, IRGACURE (registered trademark) 2959, and IRGACURE (registered trademark) 127 (trade names, all manufactured by BASF); aminoacetophenone-based initiators such as IRGACURE (registered trademark) 907, IRGACURE (registered trademark) 369, and IRGACURE (registered trademark) 379 (trade names, all manufactured by BASF); and acylphosphine-based initiators such as IRGACURE (registered trademark) 819 and DAROCUR (registered trademark) TPO (trade names, both manufactured by BASF).

As the photopolymerization initiator an oxime compound is preferable.

Specific examples of the oxime compound include compounds described in JP2001-233842A, compounds described in JP2000-80068A, compounds described in JP2006-342166A, and compounds described in paragraphs 0073 to 0075 of JP2016-6475A. In addition, among the oxime compounds, the photopolymerization initiator is preferably an oxime ester compound, and examples of a commercially available product on the market include IRGACURE-OXE01 and IRGACURE-OXE02 (both manufactured by BASF).

Examples of a cationic polymerization initiator include an initiator for initiating photocationic polymerization, a light-decoloring agent for a coloring agent compound, a photochromic agent, a known acid generator used in a microresist, and a mixture thereof. Specific examples of the cationic polymerization initiator include onium compounds, organic halogen compounds, and disulfone compounds.

Examples of the onium compound include a diazonium salt, an ammonium salt, an iminium salt, a phosphonium salt, an iodonium salt, a sulfonium salt, an arsonium salt, and a selenium salt. In addition, examples of the onium compound include compounds described in paragraphs 0058 and 0059 of JP2002-29162A.

In a case of including a polymerization initiator, the liquid composition according to the embodiment of the present disclosure may include the polymerization initiator alone or in combination of two or more kinds thereof.

In a case where the liquid composition according to the embodiment of the present disclosure includes the polymerization initiator, the content of the polymerization initiator in the liquid composition is preferably 0.1% by mass to 20% by mass, more preferably 0.3% by mass to 15% by mass, and still more preferably 0.4% by mass to 10% by mass with respect to the total solid content of the liquid composition.

The liquid composition according to the embodiment of the present disclosure can be prepared by mixing the coloring agent represented by Formula 1 (that is, the specific coloring agent) and the solvent, and as necessary, the polymerizable compound, the polymerization initiator, the ultraviolet absorber, and other components.

<Coloring Agent Compound>

The coloring agent compound according to the embodiment of the present disclosure is a coloring agent compound represented by Formula 2.

The coloring agent compound represented by Formula 2 represents a part of the coloring agent represented by Formula 1, and the compound in the range represented by Formula 2 is a novel coloring agent compound.

Formula 2

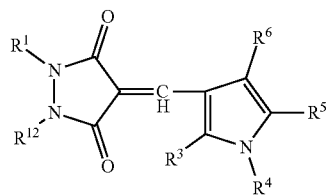

In Formula 2, $R^1$ represents an alkyl group or an aryl group.

The alkyl group or aryl group in $R^1$ of Formula 2 is synonymous with the alkyl group or aryl group in $R^1$ of Formula 1, and preferred aspects thereof are also the same.

In a case where $R^1$ represents an alkyl group, $R^{12}$ represents an alkyl group or an aryl group, $R^3$, $R^5$, and $R^6$ each independently represent a hydrogen atom, an alkyl group, or an aryl group, $R^4$ represents a hydrogen atom, an alkyl group, an aryl group, or an amino group, and $R^5$ and $R^6$ may be bonded to each other to form a 6-membered ring.

On the other hand, in a case where $R^1$ represents an aryl group, $R^{12}$ represents an aryl group, $R^3$, $R^5$, and $R^6$ each independently represent a hydrogen atom, an alkyl group, or an aryl group, at least one of $R^3$ or $R^6$ represents a hydrogen atom, $R^4$ represents a hydrogen atom, an alkyl group, an aryl group, or an amino group, and $R^5$ and $R^6$ may be bonded to each other to form a 6-membered ring. However, a case where the aryl group in $R^1$ and $R^{12}$ is substituted with a group having a sulfonamide structure (—$SO_2NH$—) is excluded.

The group having a sulfonamide structure refers to a sulfonamide group or a substitute thereof.

In a case where $R^1$ and $R^{12}$ represent an aryl group, it is preferable that the aryl groups in $R^1$ and $R^{12}$ do not include an aryl group substituted with a dissociable group.

The dissociable group refers to a group in which a hydrogen atom can be removed and ionized, and the dissociable group includes a group having a sulfonamide structure, a sulfo group, a phosphonic acid group, a carboxy group, a hydroxy group, and the like.

In particular, from the viewpoint of light resistance, it is preferable that $R^1$ of $R^1$ and $R^{12}$ in Formula 2 is an alkyl group. For the same reason, it is more preferable that both $R^1$ and $R^{12}$ independently represent an alkyl group, and it is still more preferable that both $R^1$ and $R^{12}$ independently represent an alkyl group having 1 to 8 carbon atoms.

The alkyl group and aryl group in $R^{12}$ of Formula 2 are synonymous with the alkyl group and aryl group in $R^2$ of Formula 1, and preferred aspects thereof are also the same.

The alkyl group and aryl group in $R^3$, $R^5$, and $R^6$ of Formula 2 are synonymous with the alkyl group and aryl group in $R^3$, $R^5$, and $R^6$ of Formula 1, respectively, and preferred aspects thereof are also the same.

The alkyl group, aryl group, and amino group in $R^4$ of Formula 2 are synonymous with the alkyl group, aryl group, and amino group in $R^4$ of Formula 1, and preferred aspects thereof are also the same.

In addition, the 6-membered ring formed by bonding $R^5$ and $R^6$ of Formula 2 to each other is synonymous with the 6-membered ring formed by bonding $R^5$ and $R^6$ of Formula 1 to each other, and preferred aspects thereof are also the same.

Specific examples of the coloring agent compound represented by Formula 2 include compounds included in the range represented by Formula 2, among the above-described compounds mentioned as specific examples of the coloring agent represented by Formula 1.

However, in the present disclosure, the coloring agent compound represented by Formula 2 is not limited to the compounds shown in the specific examples.

The coloring agent compound represented by Formula 2 can be synthesized by, as shown in the scheme described in the section of the resin composition described above, mixing pyrazolidinedione represented by Formula 3 and an aldehyde represented by Formula 4 in an organic solvent under the conditions of room temperature (that is, 25° C.) or reflux.

Details of the temperature and time during reflux, the organic solvent, the catalyst, and the cooling and washing after reflux are the same as in the case of the coloring agent represented by Formula 1, and thus the description thereof will be omitted here.

<Optical Material>

The optical material according to the embodiment of the present disclosure is a cured substance of the resin composition or liquid composition according to the embodiment of the present disclosure described above.

Therefore, the optical material according to the embodiment of the present disclosure includes at least the coloring agent represented by Formula 1 (that is, the specific coloring agent) described above. Accordingly, in the optical material according to the embodiment of the present disclosure, blocking property in a wavelength range of at least 350 nm to 450 nm is excellent, and light resistance and heat resistance are also excellent.

The "cured substance" in the present disclosure includes a dried substance obtained by drying and solidifying the resin composition or the liquid composition, and a cured substance obtained by curing the resin composition or the liquid composition in a case where the resin composition or the liquid composition undergoes a curing reaction.

Examples of the optical material include an optical filter (for example, an optical lens), and an optical film or an optical sheet (for example, film for windows of vehicles or houses, film for display of various image display apparatuses (LCD, organic EL element, and the like) or portable terminals (smartphones, tablets, and the like), and film for organic solar cells). The optical film or optical sheet includes a protective film or protective sheet for imparting a protective function.

The optical material may be obtained as a molded product obtained by molding the resin composition into a desired shape. That is, the optical material may be a molded product formed of the resin composition or the liquid composition.

For example, in a case where the optical material is an optical lens (for example, a spectacle lens), the optical lens may be obtained by molding the resin composition into a lens shape.

In addition, the optical material may have a transparent supporting base material and a resin layer laminated. In this case, at least one of the supporting base material or the resin layer is formed of the resin composition or the liquid composition.

For example, the optical material may be an optical film or optical sheet having a transparent supporting base material and a coloring agent-containing layer (so-called resin layer) containing the specific coloring agent laminated, or a protective film or protective sheet having a transparent supporting base material, a hardcoat layer, and an adhesion layer or adhesive layer laminated. In a case where the optical material is a protective film or a protective sheet, it is sufficient that the specific coloring agent is included in at least one of the supporting base material, the hardcoat layer, or the adhesion layer or adhesive layer. In a case where the optical material is a protective film or a protective sheet, for example, a form of the protective film or the protective sheet may be a form in which the adhesive layer disposed on the supporting base material includes the specific coloring agent, and the adhesion layer or adhesive layer has both an ultraviolet ray and blue light blocking function and an adhesion function or adhesive function.

Details and preferred aspects of the coloring agent represented by Formula 1 (that is, the specific coloring agent) and the resin, and the components other than the specific coloring agent and the resin included in the optical material are the same as those of the resin composition described above, and thus detailed description thereof will be omitted here.

Embodiments of the optical material will be described.

First Embodiment of Optical Material

A first embodiment is an optical material having a transparent supporting base material and a resin layer laminated.

Examples of the optical material of the first embodiment include an optical film or an optical sheet, and a protective film or a protective sheet.

—Supporting Base Material—

The supporting base material preferably has transparency as long as the optical performance is not impaired.

The fact that the supporting base material is transparent means that the supporting base material is optically transparent, and specifically, means that the total light transmittance of the supporting base material is 85% or more.

The total light transmittance of the supporting base material is preferably 90% or more, and more preferably 95% or more.

The total light transmittance of the supporting base material is a value determined from measured values obtained by measuring the spectral spectrum of the supporting base material using a UV/vis spectrum meter (for example, UV/vis spectrum meter UV3400 manufactured by Shimadzu Corporation).

Suitable examples of the supporting base material include a resin film.

Examples of a resin forming the supporting base material include ester resins (for example, polyethylene terephthalate (PET), polyethylene naphthalate (PEN), polybutylene terephthalate (PBT), and polycyclohexanedimethylene terephthalate (PCT)), olefin resins (for example, polypropylene (PP) and polyethylene (PE)), polyvinyl chloride (PVA), and cellulose triacetate (TAC).

Among these, from the viewpoint of general-purpose properties, PET is preferable as the resin forming the supporting base material.

The supporting base material is obtained by molding the above-described resin into a plate shape by a conventional method. In addition, as the supporting base material, a commercially available resin film on the market, or the like may be used.

The thickness of the supporting base material can be appropriately selected depending on the intended use or purpose. Generally, the thickness of the supporting base material is preferably 5 m to 2500 m and more preferably 20 m to 500 m.

—Resin Layer—

The resin layer is a layer formed by using the resin composition according to the embodiment of the present disclosure described above, or the liquid composition according to the embodiment of the present disclosure in a case of including the resin.

The resin layer may be a layer which has been dried and solidified, or may be a cured layer obtained by a curing reaction.

The thickness of the resin layer is not particularly limited, but from the viewpoint of absorbance in a wavelength range of 350 nm to 450 nm (in other words, for example, the content of the specific coloring agent) and desired visible light transmittance, the thickness thereof can be optionally selected.

The thickness of the resin layer may be, for example, 5 m to 2500 m.

In particular, from the viewpoint of being superior in the function of blocking or suppressing ultraviolet rays and blue light, and from the viewpoint of being easy to secure visible light transmittance and easy to handle, the thickness of the resin layer is preferably 5 m to 500 m and more preferably 5 m to 100 μm.

~Formation of Resin Layer~

The resin layer can be formed by applying (and optionally curing) the resin composition or liquid composition according to the embodiment of the present disclosure prepared as a coating liquid to a desired region of the supporting base material.

In a case where the resin composition or the liquid composition has curing properties, by applying energy after coating and causing a curing reaction, a resin layer which is a cured substance of the resin composition or the liquid composition is formed.

After the coating (in a case of curing, before curing), the coating film formed by coating may be dried.

The coating film can be dried by a known method such as a method of blowing hot air, a method of passing through a drying zone controlled to a predetermined temperature, and a method of heating with a heater provided in a transport roll.

Energy can be applied by irradiation with visible light, ultraviolet rays (UV), electron beams, and the like, or heating. Among these, as the energy applying, irradiation with visible light or ultraviolet rays is preferable, and irradiation with ultraviolet rays is more preferable.

From the viewpoint of improving the curing properties, it is preferable to, before curing by applying energy, dry the coating film in advance to reduce the amount of the solvent in the film. The drying here can be performed in the same manner as described above.

The energy can be applied by irradiating light, for example, using a light source capable of UV irradiation. As the light source, for example, an ultrahigh pressure UV lamp (for example, an ultrahigh pressure mercury lamp) and a UV light emitting diode (UV-LED) can be used.

From the viewpoint that the curing reaction proceeds well, the irradiation amount is preferably in a range of 10 mJ/cm$^2$ to 1000 mJ/cm$^2$.

In a case where the curing reaction is performed by irradiation with UV or the like, from the viewpoint of suppressing curing inhabitation by oxygen and further promoting surface hardening of the resin layer, it is preferable to replace the atmosphere in a UV irradiation region with an inert gas (for example, nitrogen gas) to reduce the oxygen concentration. The oxygen concentration in the atmosphere of the UV irradiation region is preferably 0.01% to 5%.

In addition, from the viewpoint of promoting the curing reaction, it is preferable to increase the temperature of the atmosphere in the UV irradiation region. The atmospheric temperature in the UV irradiation region is preferably 25° C. to 100° C., more preferably 30° C. to 80° C., and still more preferably 40° C. to 70° C.

Second Embodiment of Optical Material

A second embodiment is an optical material having a hardcoat layer, a transparent supporting base material, and a pressure-sensitive adhesive layer or adhesive layer laminated in this order.

Examples of the optical material of the second embodiment include a protective film and a protective sheet.

In the second embodiment, any of the supporting base material, the hardcoat layer, or the pressure-sensitive adhesive layer or adhesive layer may include the specific coloring agent, or two or more of the supporting base material, the hardcoat layer, and the pressure-sensitive adhesive layer or adhesive layer may include the specific coloring agent.

That is, in the second embodiment, at least one of the supporting base material, the hard coat layer, or the pressure-sensitive adhesive layer or adhesive layer is formed by using the resin composition or liquid composition according to the embodiment of the present disclosure.

The second embodiment is preferably an aspect (1) in which at least the hardcoat layer is a cured substance of the resin composition or liquid composition according to the embodiment of the present disclosure, or an aspect (2) in which at least the supporting base material is a cured substance of the resin composition or liquid composition according to the embodiment of the present disclosure. The supporting base material in the case of (1) is synonymous with the first embodiment, except that the supporting base material may include the specific coloring agent, and the supporting base material in the case of (2) is a cured substance formed by using the resin composition or liquid composition according to the embodiment of the present disclosure.

—Hardcoat Layer—

The second embodiment has a hardcoat layer on the supporting base material.

In a case where the optical material has the hardcoat layer as the outermost layer, scratch resistance of the optical material can be improved.

The hardcoat layer may be formed by either a wet coating method or a dry coating method (vacuum film formation). As a method for forming the hardcoat layer, a wet coating method is preferable from the viewpoint that it is excellent in productivity. In a case where the hardcoat layer is formed by using the resin composition or liquid composition according to the embodiment of the present disclosure, the hardcoat layer is formed by the wet coating method.

In a case where the hardcoat layer is not the cured substance of the resin composition or liquid composition according to the embodiment of the present disclosure, as the hardcoat layer, for example, hardcoat layers described in JP2013-45045A, JP2013-43352A, JP2012-232459A, JP2012-128157A, JP2011-131409A, JP2011-131404A, JP2011-126162A, JP2011-75705A, JP2009-286981A, JP2009-263567A, JP2009-75248A, JP2007-164206A, JP2006-96811A, JP2004-75970A, JP2002-156505A, JP2001-272503A, WO2012/018087A, WO2012/098967A, WO2012/086659A, and WO2011/105594A can be applied.

In a case where the optical material has a hardcoat layer, from the viewpoint of scratch resistance of the optical material, the thickness of the hardcoat layer is preferably 5 m to 100 m.

—Pressure-Sensitive Adhesive Layer or Adhesive Layer—

The second embodiment is an optical material having a pressure-sensitive adhesive layer or adhesive layer on the side opposite to the side of the supporting base material having the hardcoat layer.

The type of a pressure sensitive adhesive or adhesive used for the pressure-sensitive adhesive layer or adhesive layer is not particularly limited.

Examples of the pressure sensitive adhesive include an acrylic pressure sensitive adhesive, a rubber-based pressure sensitive adhesive, and a silicone-based pressure sensitive adhesive. The acrylic pressure sensitive adhesive refers to a pressure sensitive adhesive including a polymer of a (meth) acrylic monomer (so-called (meth)acrylicpolymer).

Examples of the adhesive include a urethane resin adhesive, a polyester adhesive, an acrylic resin adhesive, an ethylene vinyl acetate resin adhesive, a polyvinyl alcohol adhesive, a polyamide adhesive, and a silicone adhesive. Among these, as the adhesive, from the viewpoint of high adhesive force, a urethane resin adhesive or a silicone adhesive is preferable.

As the adhesive, a commercially available product on the market may be used, and examples of the commercially available product include a urethane resin-based adhesive (trade name: LIS-073-50U) of TOYO INK CO., LTD. As the adhesive, for example, a curing agent (trade name: CR-001) of TOYO INK CO., LTD. may be used in combination.

In a case where the optical material has a pressure-sensitive adhesive layer or adhesive layer, from the viewpoint of achieving both pressure sensitive adhesive force and handleability, the thickness of the pressure sensitive adhesive layer or adhesive layer is preferably 5 m to 100 m.

EXAMPLES

Hereinafter, the present invention will be described in more detail using examples. However, the present invention is not limited to the following examples as long as it does not depart from the gist of the present invention.

(Example 1): Synthesis Example (Synthesis of D-13)

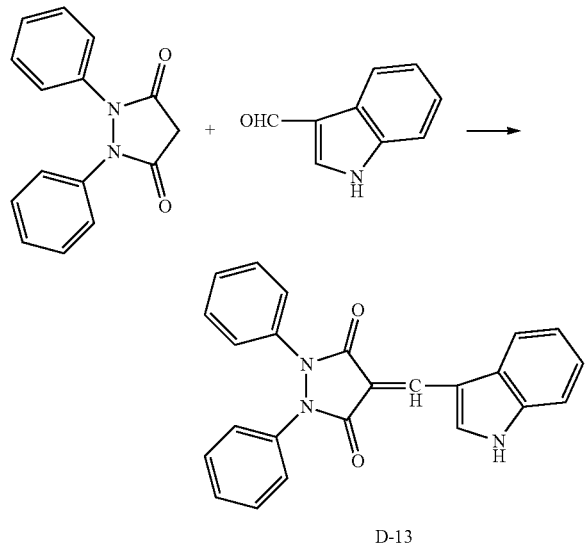

According to the above-described scheme, 5.0 g of 1,2-diphenylpyrazolidin-3,5-dione, 3.2 g of indole-3-carboxyaldehyde, 0.3 g of ammonium acetate, and 70 ml of methanol were added and heated under reflux for 2 hours. After completion of the reaction, the reactant was cooled to room temperature (that is, 25° C.), and the precipitated solid was filtered and washed with methanol to obtain 6.6 g of a compound D-13 (yield: 87%).

A result of confirming the structure of the compound D-13 by nuclear magnetic resonance (NMR) is shown below.

$^1$H-NMR (CDCl$_3$): δ 9.86 (s, 1H), 9.64 (s, 1H), 8.56 (s, 1H), 7.97 (d, 1H), 7.50 to 7.46 (m, 4H), 7.39 to 7.37 (m, 7H), 7.31 to 7.14 (m, 2H)

The obtained compound D-13 was dissolved in ethyl acetate, and the maximum absorption wavelength (λmax) and molar absorption coefficient (E) thereof were measured using a cell having an optical path length of 10 mm and using a spectrophotometer UV-1800PC (manufactured by Shimadzu Corporation).

As a result, the maximum absorption wavelength (λmax) of the compound D-13 was 421 nm, and the molar absorption coefficient (E) was 41400.

(Example 2): Synthesis Example (Synthesis of D-14)

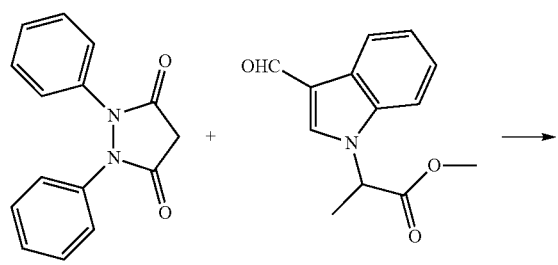

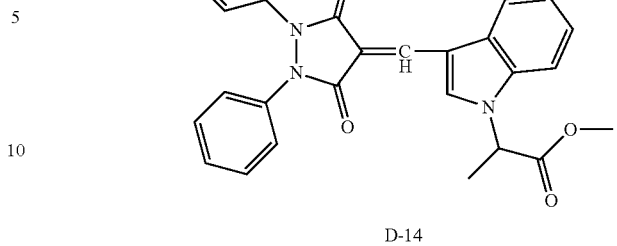

A compound D-14 was obtained by reacting in the same manner as in the synthesis of the compound D-13, except that, in the synthesis of the compound D-13 of Example 1, indole-3-carboxyaldehyde was changed to methyl 2-(3-formyl-1H-indol-1-yl)propanoate.

A result of confirming the structure of the compound D-14 by NMR is shown below.

$^1$H-NMR (CDCl$_3$): δ 9.90 (s, 1H), 8.52 (s, 1H), 8.01 to 7.99 (m, 1H), 7.47 to 7.31 (m, 11H), 7.18 to 7.13 (m, 2H), 5.25 to 5.22 (m, 1H), 3.73 (s, 3H), 1.98 (d, 3H)

The maximum absorption wavelength (λmax) and molar absorption coefficient (ε) of the obtained compound D-14 were measured in the same manner as in Example 1. Measurement results of the maximum absorption wavelength (λmax) and molar absorption coefficient (ε) are shown in Table 1 below.

(Example 3): Synthesis Example (Synthesis of D-24)

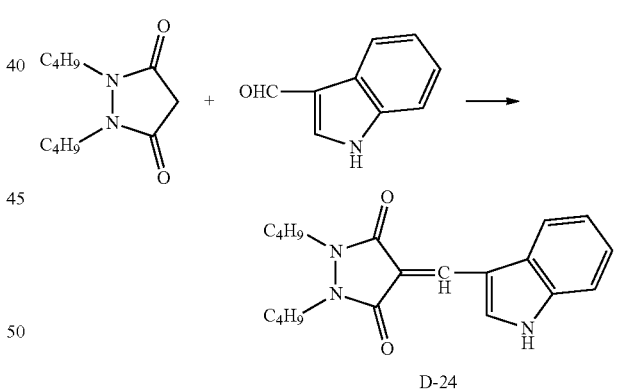

A compound D-24 was obtained by reacting in the same manner as in the compound D-13, except that, in the synthesis of the compound D-13 of Example 1, 1,2-diphenylpyrazolidin-3,5-dione was changed to 1,2-dibutylpyrazolidin-3,5-dione. A result of confirming the structure of the compound D-24 by NMR is shown below.

$^1$H-NMR (CDCl$_3$): δ 9.76 (s, 1H), 9.30 (s, 1H), 8.33 (s, 1H), 7.96 to 7.95 (m, 1H), 7.48 to 7.47 (m, 1H), 7.35 to 7.33 (m, 2H), 3.41 (t, 4H), 1.67 to 1.65 (m, 4H), 1.35 to 0.31 (m, 4H), 0.95 to 0.91 (m, 6H)

The maximum absorption wavelength (λmax) and molar absorption coefficient (ε) of the obtained compound D-24 were measured in the same manner as in Example 1.

Measurement results of the maximum absorption wavelength (λmax) and molar absorption coefficient (ε) are shown in Table 1 below.

(Example 4): Synthesis Example (Synthesis of D-4)

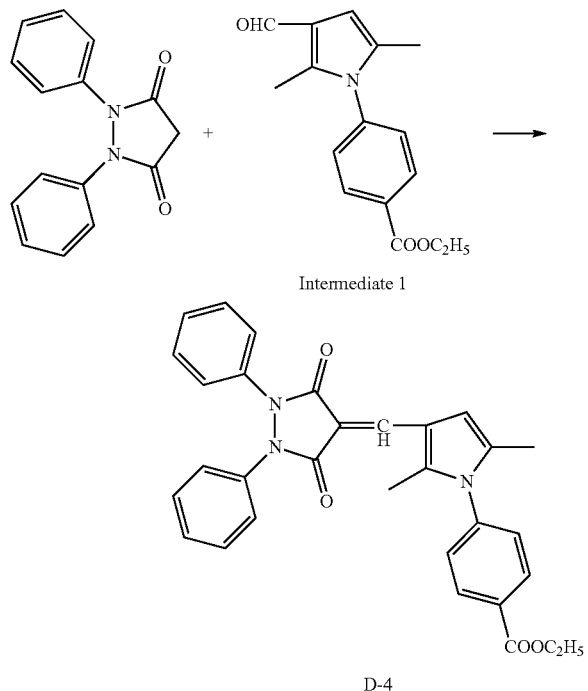

Intermediate 1

D-4

A compound D-4 was obtained by reacting in the same manner as in the compound D-13, except that, in the synthesis of the compound D-13 of Example 1, indole-3-carboxyaldehyde was changed to an intermediate 1 (synthesized by the method described in JP2707371B).

A result of confirming the structure of the compound D-4 by NMR is shown below.

$^1$H-NMR (CDCl$_3$): δ 8.23 (d, 2H), 8.09 (s, 1H), 7.82 (s, 1H), 7.46 to 7.44 (m, 4H), 7.35 to 7.30 (m, 6H), 7.17 to 7.12 (m, 2H), 4.46 to 4.41 (m, 2H), 2.30 (s, 3H), 2.01 (s, 3H), 1.43 (t, 3H)

The maximum absorption wavelength (λmax) and molar absorption coefficient (ε) of the obtained compound D-4 were measured in the same manner as in Example 1. Measurement results of the maximum absorption wavelength (λmax) and molar absorption coefficient (ε) are shown in Table 1 below.

(Example 5): Synthesis Example (Synthesis of D-10)

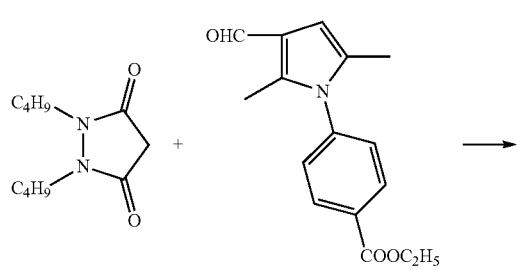

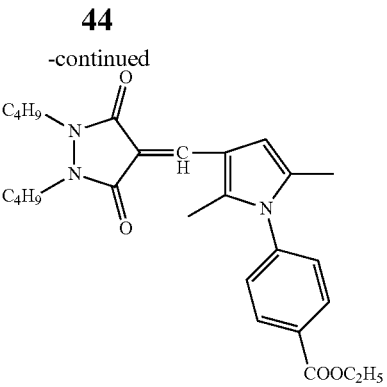

D-10

A compound D-10 was obtained by reacting in the same manner as in the compound D-4, except that, in the synthesis of the compound D-4 of Example 4, 1,2-diphenylpyrazolidin-3,5-dione was changed to 1,2-dibutylpyrazolidin-3,5-dione.

A result of confirming the structure of the compound D-10 by NMR is shown below.

$^1$H-NMR (CDCl$_3$): δ 8.21 (d, 2H), 7.86 (s, 1H), 7.78 (s, 1H), 7.29 (s, 1H), 4.44 to 4.41 (m, 2H), 3.67 to 3.66 (m, 4H), 2.26 (s, 3H), 2.02 (s, 3H), 1.58 to 1.54 (m, 4H), 1.45 to 1.41 (m, 3H), 1.36 to 1.32, (m, 4H), 0.94 to 0.90 (m, 6H)

The maximum absorption wavelength (λmax) and molar absorption coefficient (ε) of the obtained compound D-10 were measured in the same manner as in Example 1. Measurement results of the maximum absorption wavelength (λmax) and molar absorption coefficient (ε) are shown in Table 1 below.

TABLE 1

| Specific coloring agent | λmax (nm) | ε |
|---|---|---|
| D-1 | 400 | 40800 |
| D-4 | 400 | 41200 |
| D-9 | 386 | 34000 |
| D-10 | 385 | 33000 |
| D-13 | 421 | 41400 |
| D-14 | 425 | 39800 |
| D-24 | 403 | 30500 |

Compounds D-1 and D-9 in Table 1 were synthesized by reacting in the same manner as in Example 1, in which 1,2-diphenylpyrazolidin-3,5-dione and indole-3-carboxyaldehyde used in the synthesis of the compound D-13 of Example 1 were changed to compounds corresponding to the compound D-1 or D-9, respectively.

(Example 6): Resin Composition

A resin solution (that is, a resin composition) in which 5.4 mg of the compound D-1, 7.6 g of chloroform, and 1.1 g of a commercially available polymethylmethacrylate resin (Dianal BR-80 (PMMA polymer containing 60 mass % or more of methylmethacrylate as a monomer unit, Mw: 95,000, acid value: 0 mgKOH/g), manufactured by Mitsubishi Rayon Co., Ltd.) were dissolved was prepared. The prepared resin solution was spin-coated on a glass substrate, and the coating film was dried at 40° C. for 2 minutes to form a resin film having a thickness of 10 m and including the compound D-1.

(Examples 7 to 12): Resin Composition

Resin films were formed in the same manner as in Example 6, except that, in Example 6, the compound D-1 was replaced with a coloring agent (that is, the specific coloring agent) shown in Table 2 below.

(Comparative Example 1): Resin Composition

A resin film was formed in the same manner as in Example 6, except that, in Example 6, the compound D-1 was replaced with the following comparative coloring agent E-1.

E-1

[Chemical structure of E-1: isoxazolone ring with tert-butyl group connected via =CH- to a 2,5-dimethylpyrrole bearing an N-(4-ethoxycarbonylphenyl) group, with COOEt label]

(Evaluation)
—1. Heat Resistance—

With regard to the resin films formed in Examples 6 to 12 and Comparative Example 1, under the following conditions 1 and 2, a retention rate of absorbance at λmax (maximum absorption wavelength; nm) was obtained, and the retention rate was used as an indicator for evaluating heat resistance. The retention rate of absorbance is shown in Table 2. As the retention rate of absorbance is larger, the heat resistance is better. The absorbance was obtained from the transmittance of wavelength light of λmax applied to the resin film using a spectrophotometer UV-1800PC (manufactured by Shimadzu Corporation).

(Condition 1)

After measuring the absorbance of the resin film at λmax, the resin film was heated at 80° C. for 1 hour (h), and the absorbance at λmax after heating was measured. The retention rate (%) of absorbance was calculated with the value of absorbance at λmax before and after heating from the following expression.

Retention rate(%) of absorbance=(Absorbance at λmax after heating/Absorbance at λmax before heating)×100

(Condition 2)

The retention rate (%) of absorbance was calculated in the same manner as in Condition 1, except that the heating condition of the resin film was changed to 200° C. for 5 minutes.

—2. Light Resistance—

With regard to the resin films formed in Examples 6 to 12 and Comparative Example 1, under the following condition 3, a retention rate of absorbance at λmax (maximum absorption wavelength; nm) was obtained, and the retention rate was used as an indicator for evaluating light resistance.

Specifically, after measuring the absorbance of the resin film at λmax, the resin film was irradiated under the condition 3, and the absorbance at λmax after irradiation for 24 hours was measured. The retention rate (%) of absorbance was calculated with the value of absorbance at λmax before and after irradiation from the following expression. The retention rate of absorbance is shown in Table 2. The absorbance was obtained from the transmittance of wavelength light of λmax applied to the resin film using a spectrophotometer UV-1800PC (manufactured by Shimadzu Corporation).

Retention rate(%) of absorbance=(Absorbance at λmax after irradiation/Absorbance at λmax before irradiation)×100

As the retention rate of absorbance is larger, the light resistance is better.

(Condition 3)
Equipment: low temperature cycle xenon weather meter (product name: XL75, manufactured by Suga Test Instruments Co., Ltd.)
Illuminance: 10 klx (40 w/m$^2$)
Time: 24 hours
Environment: 23° C., 5% RH
Measurement: λmax measurement through an ultraviolet cut filter which cuts wavelengths of 320 nm or less

TABLE 2

| | Coloring agent type | Heat resistance | | Light resistance 1 day |
|---|---|---|---|---|
| | | 80° C./ 1 h | 200° C./ 5 min | |
| Example 6 | D-1 | 100% | 98% | 95% |
| Example 7 | D-4 | 100% | 98% | 93% |
| Example 8 | D-9 | 100% | 97% | 98% |
| Example 9 | D-10 | 100% | 96% | 99% |
| Example 10 | D-13 | 100% | 97% | 91% |
| Example 11 | D-14 | 100% | 98% | 97% |
| Example 12 | D-24 | 100% | 92% | 99% |
| Comparative Example 1 | E-1 | 97% | 41% | 81% |

The seven specific coloring agents (that is, the coloring agent represented by Formula 1) synthesized as described above were a compound which has a maximum absorption wavelength in a wavelength range of 350 nm to 450 nm and exhibits UV blocking property and blue light blocking property.

In addition, as shown in Table 2, in Examples 6 to 12 using the specific coloring agent, the resin films formed as a molded product of the resin composition were excellent in heat resistance and light resistance. On the other hand, in Comparative Example 1 using the comparative coloring agent E-1, the formed resin film was significantly inferior in heat resistance and light resistance.

The resin composition and liquid composition according to the embodiment of the present disclosure can be applied to optical materials. The optical material includes, for example, an optical filter (for example, an optical lens) and an optical film or optical sheet (including a protective sheet).

Specific examples of the optical material include blue light cut materials which block or suppress blue light in the visible light range (such as blue a light cut lens (for example, eyeglass and contact lens)); and UV cut materials which block or suppress ultraviolet rays (UV) (such as a UV cut lens (for example, eyeglass and contact lens), a UV cut film or a UV cut sheet (for example, film for windows, film for display various image display apparatuses, and film for display of portable terminals (smartphones, tablets, and the like)). The optical material according to the embodiment of the present disclosure is suitable for, for example, applications for improving durability of LCD and organic EL element. Among these, the optical material according to the embodiment of the present disclosure is particularly suitable for applications used in an environment in which heat resistance and light resistance are required.

In addition, the liquid composition according to the embodiment of the present disclosure and the coloring agent compound according to the embodiment of the present disclosure are suitable for use in an environment in which heat resistance and light resistance are required, and can be suitably used for applications such as ink and paint.

In addition, the coloring agent compound according to the embodiment of the present disclosure can be added to a pressure sensitive adhesive for use.

Examples of the image display apparatus include a liquid crystal display device (LCD), a plasma display panel, an electroluminescence (EL) display, and a cathode tube display device.

In addition, the image display apparatus includes not only a large-area image display apparatus but also a portable terminal such as a smartphone and tablet terminal, in which a touch panel is equipped.

The touch panel is not particularly limited, and can be appropriately selected according to the purpose. Examples of the touch panel include a surface type capacitance-type touch panel, a projection type capacitance-type touch panel, and a resistive film-type touch panel. The touch panel includes a so-called touch sensor and touch pad.

The disclosure of JP2019-096563 filed on May 23, 2019 is incorporated in the present specification by reference.

All documents, patent applications, and technical standards described in the present specification are incorporated herein by reference to the same extent as in a case of being specifically and individually noted that individual documents, patent applications, and technical standards are incorporated by reference.

What is claimed is:

1. A resin composition comprising:
a coloring agent represented by Formula 1; and
a resin,

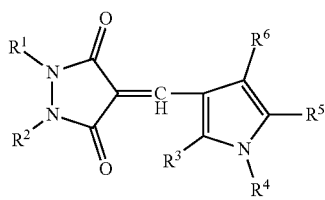

Formula 1 wherein, in Formula 1, both $R^1$ and $R^2$ represent unsubstituted phenyl groups or unsubstituted alkyl groups having 1 to 12 carbon atoms,
$R^3$, $R^5$, and $R^6$ satisfy the following (i) or (ii), (i) $R^5$ and $R^6$ are bonded to each other to form a 6-membered ring and $R^3$ represents a hydrogen atom or a substituent, or
(ii) $R^3$ and $R^5$ each independently represent an unsubstituted alkyl group having 1 to 8 carbon atoms and $R^6$ represents a hydrogen atom or a substituent, and
$R^4$ represents a hydrogen atom, a substituted alkyl group substituted with an alkoxycarbonyloxy group having totally 1 to 18 carbon atoms, or a substituted aryl group substituted with an alkoxycarbonyloxy group having totally 6 to 22 carbon atoms, provided that when $R^4$ is a hydrogen atom, both $R^1$ and $R^2$ are unsubstituted alkyl groups having 1 to 12 carbon atoms.

2. A liquid composition comprising:
a coloring agent represented by Formula 1; and
a solvent,

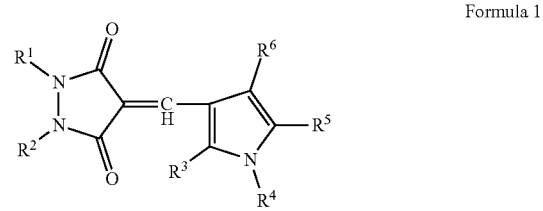

Formula 1 wherein, in Formula 1, both $R^1$ and $R^2$ represent unsubstituted phenyl groups or unsubstituted alkyl groups having 1 to 12 carbon atoms,
$R^3$, $R^5$, and $R^6$ satisfy the following (i) or (ii), (i) $R^5$ and $R^6$ are bonded to each other to form a 6-membered ring and $R^3$ represents a hydrogen atom or a substituent, or
ii) $R^3$ and $R^5$ each independently represent an unsubstituted alkyl group having 1 to 8 carbon atoms and $R^6$ represents a hydrogen atom or a substituent, and
$R^4$ represents a hydrogen atom, a substituted alkyl group substituted with an alkoxycarbonyloxy group having totally 1 to 18 carbon atoms, or a substituted aryl group substituted with an alkoxycarbonyloxy group having totally 6 to 22 carbon atoms, provided that when $R^4$ is a hydrogen atom, both $R^1$ and $R^2$ are unsubstituted alkyl groups having 1 to 12 carbon atoms.

3. The liquid composition according to claim 2, wherein the liquid composition is used for an ink or a paint.

4. A coloring agent compound represented by Formula 2,

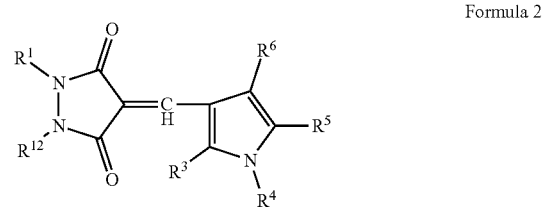

Formula 2 wherein, in Formula 2,
both $R^1$ and $R^{12}$ represent unsubstituted phenyl groups or unsubstituted alkyl groups having 1 to 12 carbon atoms,
$R^3$, $R^5$, and $R^6$ satisfy the following (i) or (ii): (i) $R^5$ and $R^6$ are bonded to each other to form a 6-membered ring and $R^3$ represents a hydrogen atom or a substituent, or
(ii) $R^3$ and $R^5$ each independently represent an unsubstituted alkyl group having 1 to 8 carbon atoms and $R^6$ represents a hydrogen atom or a substituent, and
$R^4$ represents a hydrogen atom, a substituted alkyl group substituted with an alkoxycarbonyloxy group having totally 1 to 18 carbon atoms, or a substituted aryl group substituted with an alkoxycarbonyloxy group having totally 6 to 22 carbon atoms, provided that when $R^4$ is a hydrogen atom, both $R^1$ and $R^{12}$ are unsubstituted alkyl groups having 1 to 12 carbon atoms.

5. An optical material which is a cured substance of the resin composition according to claim 1.

6. An optical material comprising:

a coloring agent represented by Formula 1,

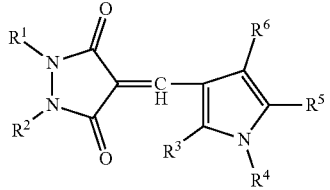

Formula 1 wherein, in Formula 1, both $R^1$ and $R^2$ represent unsubstituted phenyl groups or unsubstituted alkyl groups having 1 to 12 carbon atoms, $R^3$, $R^5$, and $R^6$ satisfy the following (i) or (ii), (i) $R^5$ and $R^6$ are bonded to each other to form a 6-membered ring and $R^3$ represents a hydrogen atom or a substituent, or (ii) $R^3$ and $R^5$ each independently represent an unsubstituted alkyl group having 1 to 8 carbon atoms and $R^6$ represents a hydrogen atom or a substituent, and $R^4$ represents a hydrogen atom, a substituted alkyl group substituted with an alkoxycarbonyloxy group having totally 1 to 18 carbon atoms, or a substituted aryl group substituted with an alkoxycarbonyloxy group having totally 6 to 22 carbon atoms, provided that when $R^4$ is a hydrogen atom, both $R^1$ and $R^2$ are unsubstituted alkyl groups having 1 to 12 carbon atoms.

7. The optical material according to claim 5, wherein the optical material is a spectacle lens.

8. The optical material according to claim 5, wherein the optical material is a protective sheet.

* * * * *